US008945923B2

(12) United States Patent
Sahin et al.

(10) Patent No.: US 8,945,923 B2
(45) Date of Patent: Feb. 3, 2015

(54) ANTIGEN-SPECIFIC CLONAL EXPANSION OF B CELLS

(75) Inventors: Ugur Sahin, Mainz (DE); Ozlem Tureci, Mainz (DE); Torsten Seppmann, Mainz (DE); Holger Hoff, Mainz (DE); Jens Schumacher, Heidelberg (DE)

(73) Assignees: BioNTech AG (DE); Universitatsmedizin der Johannes Gutenberg-Universitat (DE)

( * ) Notice: Subject to any disclaimer, the term of this patent is extended or adjusted under 35 U.S.C. 154(b) by 0 days.

(21) Appl. No.: 13/504,638

(22) PCT Filed: Oct. 29, 2010

(86) PCT No.: PCT/EP2010/006633
§ 371 (c)(1),
(2), (4) Date: Apr. 27, 2012

(87) PCT Pub. No.: WO2011/050985
PCT Pub. Date: May 5, 2011

(65) Prior Publication Data
US 2012/0219991 A1 Aug. 30, 2012

(30) Foreign Application Priority Data

Oct. 30, 2009 (EP) .................................. 09013690

(51) Int. Cl.
| A01N 1/00 | (2006.01) |
| C12N 5/00 | (2006.01) |
| C12N 5/02 | (2006.01) |
| C12N 5/10 | (2006.01) |
| C07K 14/705 | (2006.01) |

(52) U.S. Cl.
CPC ....... *C07K 14/70578* (2013.01); *C07K 2319/30* (2013.01)
USPC ........ 435/377; 435/326; 424/93.2; 424/93.21

(58) Field of Classification Search
None
See application file for complete search history.

(56) References Cited

U.S. PATENT DOCUMENTS

2006/0287229 A1 * 12/2006 Eshel et al. ..................... 514/12

FOREIGN PATENT DOCUMENTS

EP 0 434 879 7/1991

OTHER PUBLICATIONS

Attwood, Science 290:471-473 (2000).*
Skolnick et al., Trends in Biotech. 18: 34-39 (2000).*
International Search Report corresponding to International Application No. PCT/EP2010/006633, mailed Jan. 27, 2011.
Hanks et al., "Re-engineered CD40 receptor enables potent pharmacological activation of dendritic-cell cancer vaccines in vivo." Nature Medicine, vol. 11, No. 2, Jan. 23, 2005, XP002399130.
Lapteva et al., "Enhanced activation of human dendritic cells by inducible CD40 and toll-like receptor-4 Ligation." Cancer Research, vol. 67, No. 21, Nov. 2007, XP002540324.
Bancherau et al., "Long-Term Human B Cell Lines Dependent on Interleukin-4 and Antibody to CD40." Science, vol. 251, No. 4989, 1991, XP002576462.
Int'l Preliminary Exam Report for PCT/EP2010/006633 mailed May 10, 2012.

* cited by examiner

*Primary Examiner* — Phillip Gambel
(74) *Attorney, Agent, or Firm* — McAndrews, Held & Malloy, Ltd.

(57) ABSTRACT

The present invention provides recombinant proteins comprising the amino acid sequence of an intracellular segment of CD40 and an amino acid sequence mediating the association of the recombinant protein with the constant region of an immunoglobulin heavy chain. The recombinant proteins according to the present invention are useful for inducing clonal expansion of a B cell having a predetermined antigen-specificity without the need for T cell or CD40L mediated co-stimulation. Thus, the present invention provides tools for clonal expansion of B cells specific for an antigen of interest and the production of B cells secreting antibodies specific for an antigen of interest. The recombinant proteins of the present invention may also be used for generating fully human monoclonal antibodies with a predetermined antigen-specificity from the B cell repertoire of a human subject.

8 Claims, 15 Drawing Sheets

ANTIGEN-SPECIFIC CLONAL EXPANSION OF B CELLS

The present application is filed pursuant to 35 U.S.C. 371 as a U.S. National Phase application of International Patent Application No. PCT/EP2010/006633, entitled "Clonal Expansion of B Cells" which was filed Oct. 29, 2010, claiming the benefit of priority to European Patent Application No. 09013690.4, which was filed on Oct. 30, 2009. The entire text of the aforementioned applications are incorporated herein by reference in their entireties.

TECHNICAL FIELD OF THE INVENTION

The present invention is in the field of antibody production, preferably human antibody production. The present invention provides recombinant proteins that are useful for inducing clonal expansion of B cells and allow for the generation of antibody secreting B cells specific for a predetermined antigen without the need for T cell or CD40 ligand (CD40L) mediated co-stimulation. Using the recombinant proteins of the present invention it is, for example, possible to induce proliferation and differentiation to Ig secretion of B cells having a desired antigen-specificity from the B cell repertoire of a subject, preferably a human subject. Thus, the present invention provides tools for the generation of fully human monoclonal antibodies with predetermined antigen-specificity which are useful, for example, in immunotherapy such as in tumor-immunotherapy.

BACKGROUND OF THE INVENTION

Antibody-based therapies have gained importance in a variety of medical fields and have emerged as the most promising therapeutic approach in oncology. Antibodies against extracellular, cell surface associated, or secreted antigens associated with specific disease conditions are potentially of diagnostic, prognostic, and or therapeutic value. It has been shown that the therapeutic administration of monoclonal antibodies (mAb) directed against proteins associated with diseases is an effective therapy method of acute and chronic diseases such as cancers or rheumatoid arthritis. Examples for mAb targeted structures are the soluble protein tumor necrosis factor alpha (TNF-α) for rheumatoid arthritis, Crohn's disease and psoriasis (mAb preparation: Infliximab and Adalimumab), as well as the cell surface proteins CD20 for non-Hodgkin lymphoma (mAb preparation: e.g., Rituximab) and HER2/neu receptor (mAb preparation: Trastuzumab [Herceptin]) for breast cancer.

The development of the monoclonal antibody (mAb) technology represented a considerable achievement and resulted in numerous applications. However, in the field of immunotherapy, rodent mAbs have proved to be of limited use because of their strong immunogenicity in humans. Due to their low immunogenicity in patients, fully human mAbs are becoming increasingly important for the treatment of a growing number of diseases, including cancer, infectious disease, and immune disorders such as autoimmune diseases. The generation of monoclonal immunotherapeutically effective antibodies (using hybridoma or phage display techniques and subsequent chimerization and humanization, respectively), however, is time consuming and cost intensive which has prevented a broad clinical application so far.

Thus, there is a need for tools in the field of antibody-based immunotherapy which allow for the generation of fully human antibodies, preferably monoclonal antibodies, recognizing an antigen of interest in an easy, time and cost saving manner.

For full activation, B cells require two independent signals (FIG. 1). The first signal is antigen-specific and is mediated by the B cell receptor (BCR) recognizing its antigen. The BCR specifically binds the antigen and induces by receptor-clustering a signal-transduction cascade which leads to the transcriptional activation of genes associated with B cell activation. Upon BCR internalization, the antigen is processed and presented on MHC class II molecules. T cells which recognize the antigen in the context of the MHC class II molecule express CD40L on their surface and thus provide the second signal required for B cell activation, the stimulation of CD40 localized at the plasma membrane of B cells with its ligand CD40L. Activation of B cells results in the proliferation, differentiation, and antibody secretion.

The present invention provides tools for the isolation of antigen-specific B lymphocytes which is based on the antigen-specific expansion of a certain population of B lymphocytes. The present invention provides the possibility to imitate the two activation signals in vitro without the need for T cell co-stimulation. By transfection of a large number of B cells with the recombinant protein of the present invention and contacting the B cells with an antigen of interest, the B cell repertoire of a subject, for example, of a patient, can be screened for B cells having a defined antigen-specificity. The present invention allows for screening of a polyclonal B cell population and activation of monoclonal B cells and thus for the generation of antibodies, preferably human antibodies, which are specific for an antigen of interest.

SUMMARY OF THE INVENTION

In a first aspect, the present invention provides a recombinant protein comprising:
(a) the amino acid sequence of an intracellular segment of CD40 or of a variant thereof which is capable of mediating the intracellular CD40 signal transduction and
(b) an amino acid sequence mediating the association of the recombinant protein with the constant region of an immunoglobulin heavy chain, wherein the amino acid sequences under (a) and (b) are linked via
(c) an amino acid sequence comprising the amino acid sequence of a transmembrane domain.

In a preferred embodiment, the amino acid sequence mediating the association of the recombinant protein with the constant region of an immunoglobulin heavy chain comprises the amino acid sequence of a segment of an immunoglobulin constant region or a variant thereof, preferably the $C_H2$ region or the $C_H2$ and the $C_H3$ region of an immunoglobulin, preferably of IgG1.

In a preferred embodiment, the transmembrane domain is selected from the group consisting of the transmembrane domain of a B cell receptor (BCR) and the transmembrane domain of CD40.

In a further aspect, the present invention provides a polynucleotide comprising a nucleic acid sequence encoding the recombinant protein of the first aspect of the present invention. Preferably, the polynucleotide is RNA, preferably in vitro transcribed RNA (IVT RNA).

In further aspects, the present invention provides a vector comprising the polynucleotide of the present invention and a host cell comprising the polynucleotide or the vector of the present invention. In a preferred embodiment, the host cell of the present invention is a B cell, preferably a $CD19^+$ B cell, preferably a human B cell.

In further aspects, the present invention provides methods using the recombinant proteins of the present invention. In particular, the present invention provides a method for inducing clonal expansion of a B cell specific for an antigen of interest and a method for producing B cells secreting antibodies specific for an antigen of interest, said methods comprising the steps of:

(i) expressing in B cells the recombinant protein of the present invention, and
(ii) contacting the B cells of (i) with the antigen of interest, In preferred embodiments of the methods of the present invention, the B cells carry a B cell receptor (BCR) on their surface. Preferably, the B cells are CD19$^+$ B cells. It is particularly preferred that the B cells in step (i) are a mixture of B cells comprising a multitude of antigen-specificities, preferably comprising the B cell repertoire of a subject or a portion thereof. In a preferred embodiment, the B cells are harvested from a subject prior to step (i), preferably from a human subject. It is preferred that the B cells are harvested from peripheral blood of the subject, preferably by density gradient centrifugation and magnetic cell sorting.

In preferred embodiment of the methods of the present invention, the B cells are transfected with a polynucleotide comprising a nucleic acid encoding the recombinant protein of the present invention to express said protein. It is particularly preferred that the polynucleotide used for transfection of the B cells is RNA, preferably in vitro transcribed RNA (IVT RNA).

In particularly preferred embodiments of the methods of the present invention, the B cells are further contacted with cytokines, preferably with interleukin 4 (IL4) and/or interleukin 21 (IL21) in step (ii).

In preferred embodiments of the methods of the present invention, the B cells are not contacted with T cells or CD40 ligand (CD40L).

In a further aspect, the present invention provides a method for generation and clonal expansion of autoreactive B cells, i.e., B cells generating autoreactive antibodies, comprising the step of inducing clonal expansion of B cells according to the methods of the present invention, preferably using antigens for vanquishing self tolerance.

In a further aspect, the present invention provides a method for producing antibodies specific to an antigen of interest, said method comprising the steps of:

(i) inducing clonal expansion of B cells or producing B cells secreting antibodies according to the methods of the present invention, and
(ii) obtaining antibodies produced by the B cells.

In a preferred embodiment, the method of this aspect of the present invention further comprises the steps of selecting proliferating B cells, preferably selecting a clone of the proliferating B cells, and culturing said selected proliferating B cells prior to step (ii).

For full activation, B cells (1) require two independent signals. The first signal is antigen-specific and is mediated by the B cell receptor (BCR) (2) recognizing its antigen (3). The BCR specifically binds the antigen (A) and induces by receptor-clustering a signal-transduction cascade (B), which leads to the transcriptional activation of genes associated with B cell activation. The BCR is internalized (C) and traffics to an intracellular compartment called the MIIC (D), where complexes comprising newly synthesized major histocompatibility complex class II (MHC) molecules and peptides derived from antigen bound to the BCR are formed. The peptide:MHC-II complexes are transported to the cell surface, where T cells (4) recognize the antigen which is presented on MHC-II molecules (E). The recognition of the peptide:MHC-II complexes by the T cell receptor leads to T cell activation (F). The activation of T cells results in the secretion of cytokines (e.g.: IL4 and IL21) and the surface expression of CD40 ligand (CD154) thereby providing "help" to B cells (G). The CD40 ligand on T cells interacts with the CD40 receptor on the surface of B cells and induces a second, antigen-unspecific signal leading to proliferation of monoclonal B cells and production of antibodies directed to the antigen.

Figure 1:
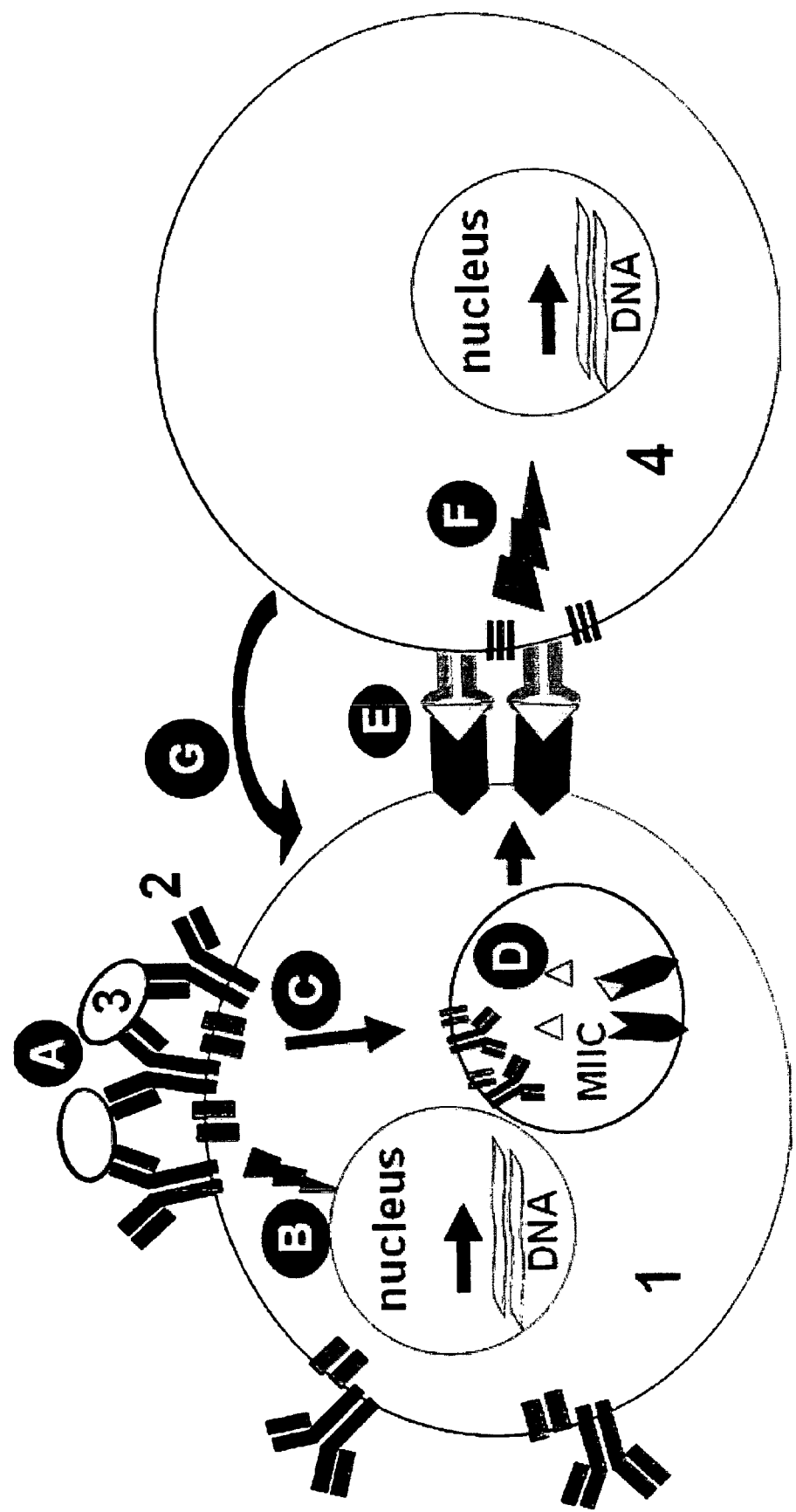
FIG. 1: Schematic representation of B cell activation.
Figure 2:
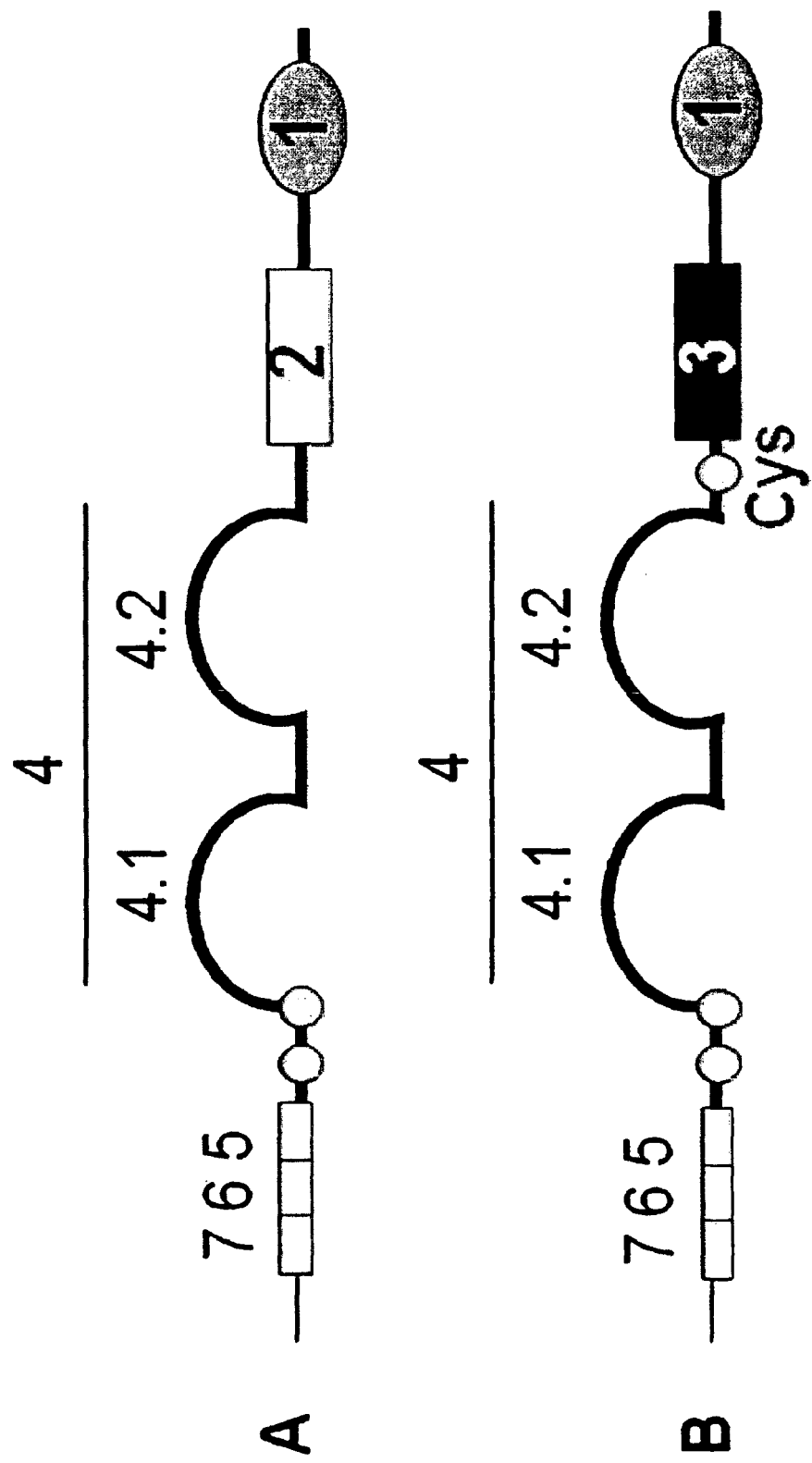

FIG. 2: Schematic representation of specific embodiments of the recombinant protein of the present invention.

Both constructs (A) and (B) comprise a C-terminal domain which is derived from the cytoplasmic domain of CD40 (1). While the construct depicted in panel (A), i.e., BZ1, carries the transmembrane (TM) domain of CD40 (2), the TM domain of the construct depicted in panel (B), i.e., BZ2, is derived from a BCR (3). The capture domain is a domain derived from human IgG1 (4) which comprises the $C_H2$ (4.1) and $C_H3$ (4.2) segments of the IgG1 heavy chain. The N-terminal part of both constructs comprises a marker domain, in particular, two c-myc epitope tags (5+7) separated by an HA-tag (6).

Figure 3:
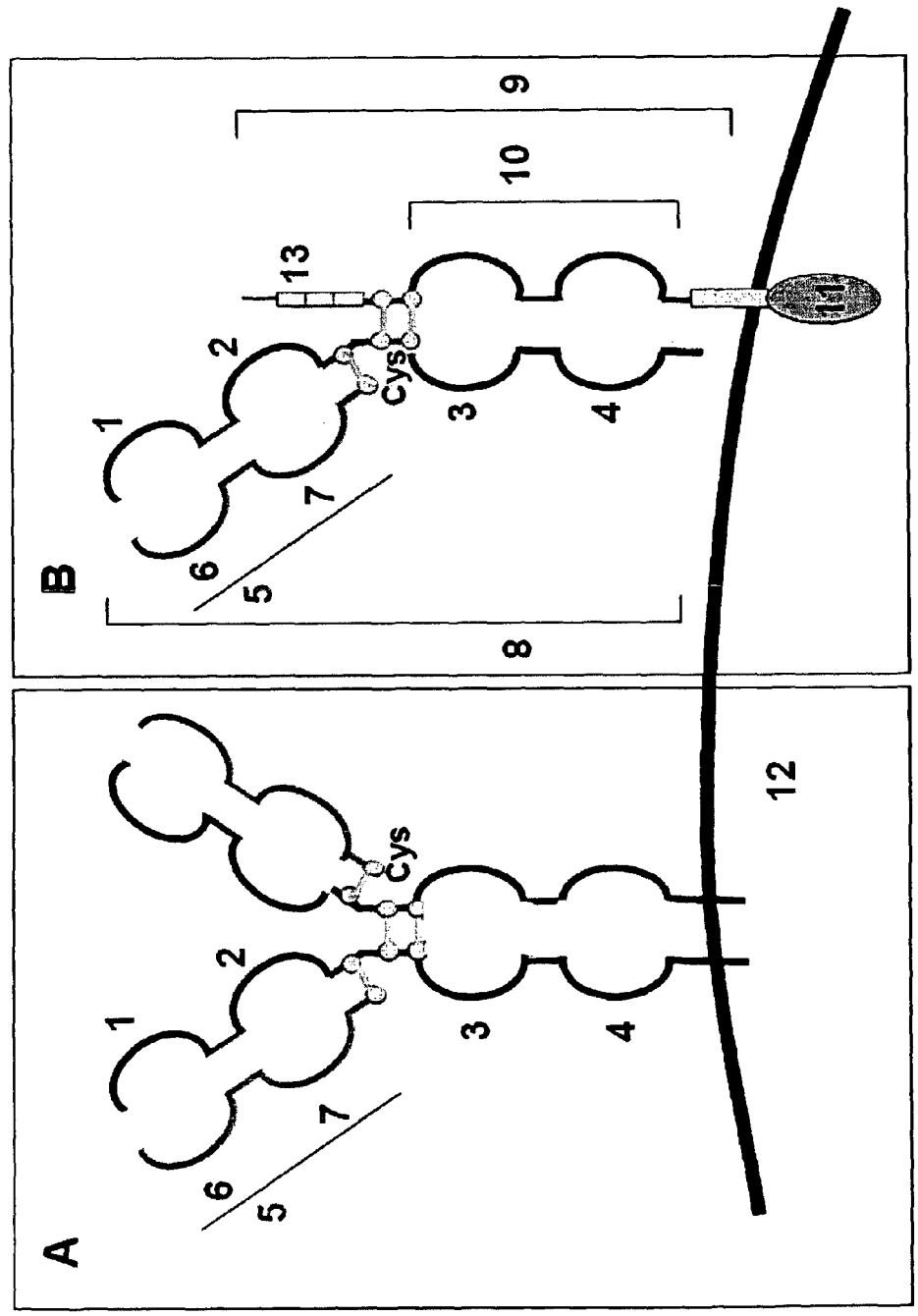

FIG. 3: Schematic representation of a BCR and the association of the recombinant protein of the present invention with a portion of an immunoglobulin.

Panel (A) depicts a normal BCR on a B cell. Panel (B) illustrates the recombinant protein of the present invention in association with a partial immunoglobulin, which is located to the plasma membrane of a B cell. The immunoglobulin heavy chain consists of a variable domain (1) and three constant domains (2+3+4) and is normally associated with a light chain (5) which consists of a variable domain (6) and a constant domain (7). A heavy chain of an immunoglobulin which is associated with an immunoglobulin light chain (8) is associated with the extracellular portion of the recombinant protein of the present invention (9). The proteins interact with each other via the immunoglobulin derived constant regions (10). The domain derived from an intracellular segment of CD40 or from a variant thereof (11) is localized intracellularly (12). An optional marker domain (13) is located within the extracellular part of the recombinant protein of the present invention and may be recognized by an antibody.

Figure 4:
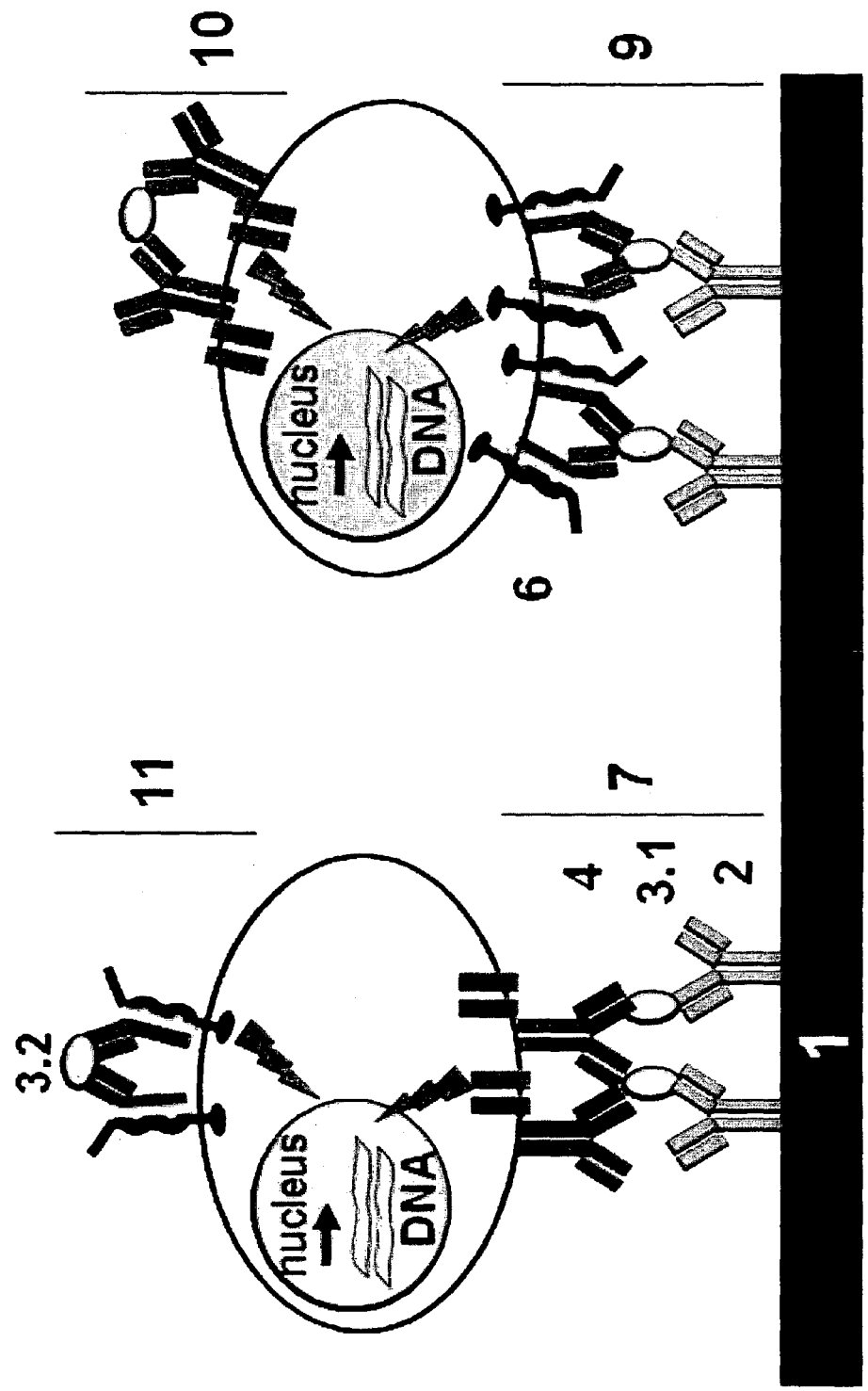

FIG. 4: Schematic representation of B cell activation using the recombinant protein of the present invention.

B cells transfected with a polynucleotide comprising a nucleic acid encoding the recombinant protein of the present invention can be antigen-specifically activated. The transfected B cells are contacted with an antigen which is recognized by the BCR (4) and the complex (6) comprising the recombinant protein of the present invention and a part of an immunoglobulin consisting of an immunoglobulin heavy and an immunoglobulin light chain. The antigen (3.1+3.2) can be applied in soluble form (10+11) or can be immobilized (7+9), for example, by directly binding to the surface of a plate or indirectly by binding to plate-bound (1) antibodies (2).

Figure 5:
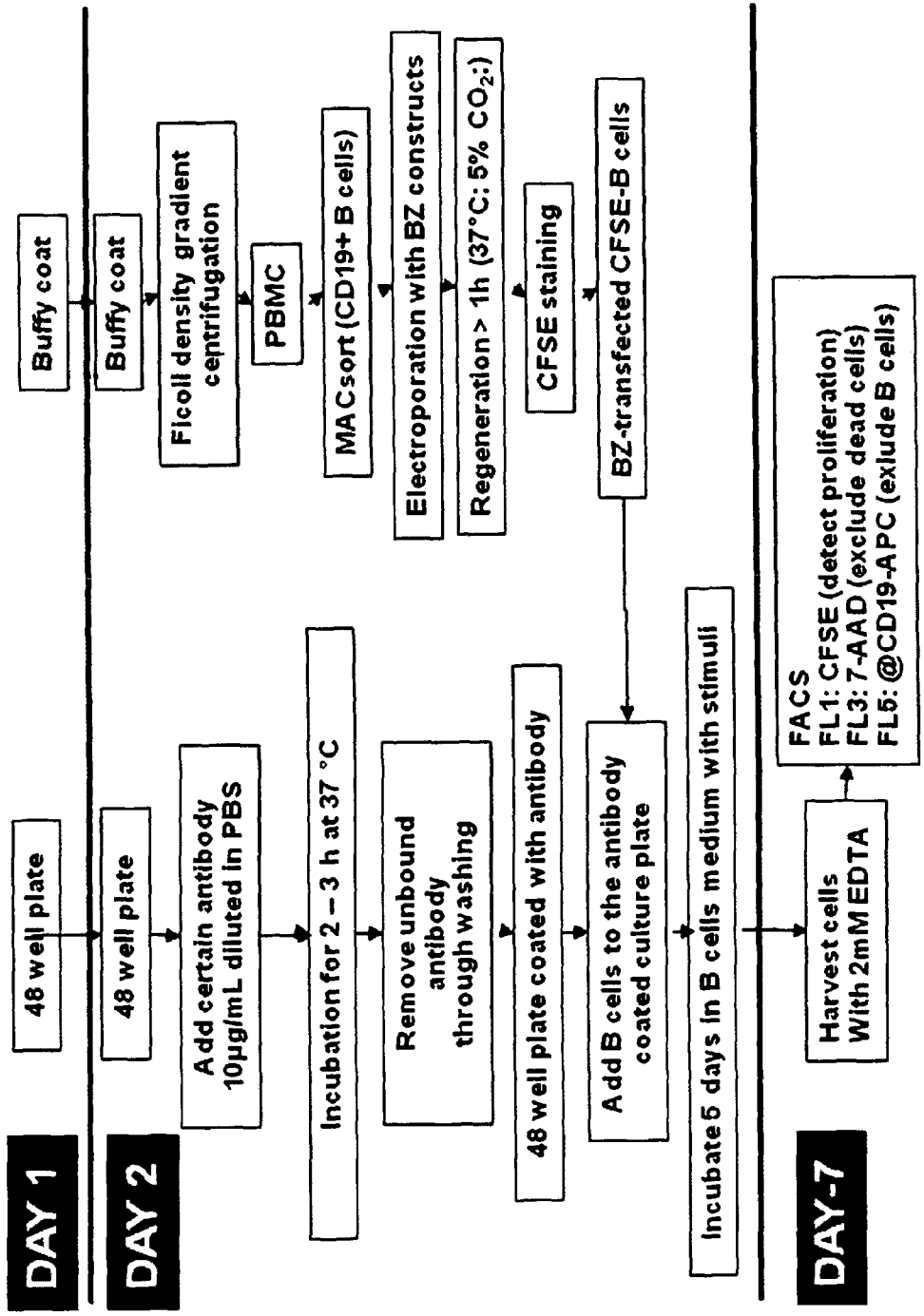

FIG. 5: Flow chart illustrating an example procedure for B cell activation using a recombinant protein of the present invention.

The left panel illustrates the preparation of the culture dish. The right panel shows the procedures for obtaining and treating B cells. BZ stands for the recombinant protein or the polynucleotide of the present invention.

Figure 6:
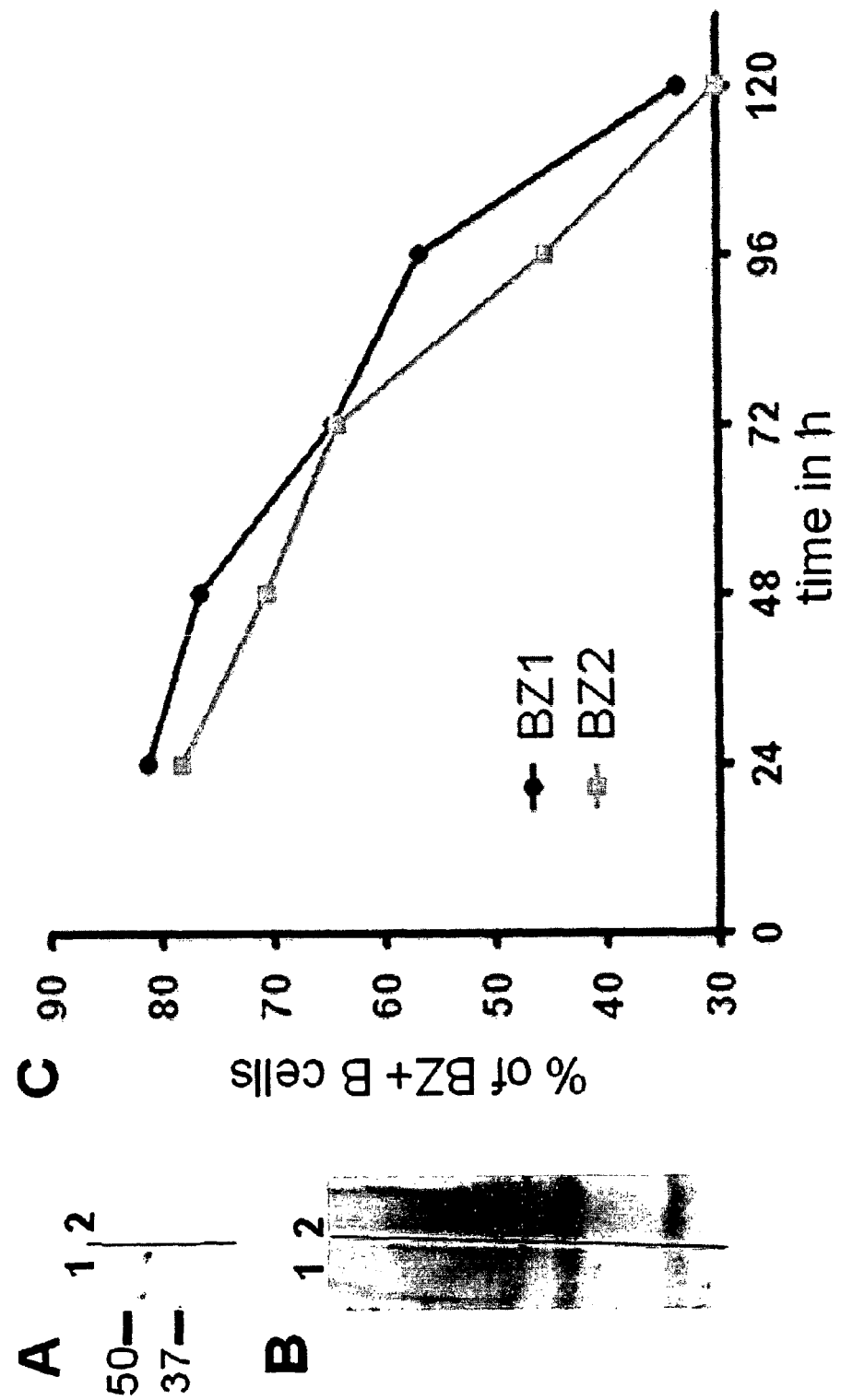

FIG. 6: Expression of a recombinant protein of the invention in primary B cells.

Panel (A) shows a Western blot analysis of a cell extract of primary B cells transfected with IVT RNA encoding a recombinant protein of the present invention. Immunostaining was performed using anti-c-myc (9E10) specific antibodies (1 μg/mL). Panel (B) shows the corresponding Coomassie staining demonstrating that an equal amount of protein was loaded for both cell extracts (1+2). 1: B cells transfected with IVT RNA encoding a recombinant protein of the present invention (SEQ ID NO: 5, BZ1); 2: non transfected B cells. Panel (C) shows the kinetics of the expression of a recombinant protein of the present invention in primary B cells. The specific embodiments of the recombinant protein of the present invention BZ1 (SEQ ID NO: 5) and BZ2 (SEQ ID NO: 6) (cf. FIG. 2) are detectable on the surface of transfected B cells over a time period of 120 hours.

Figure 7:
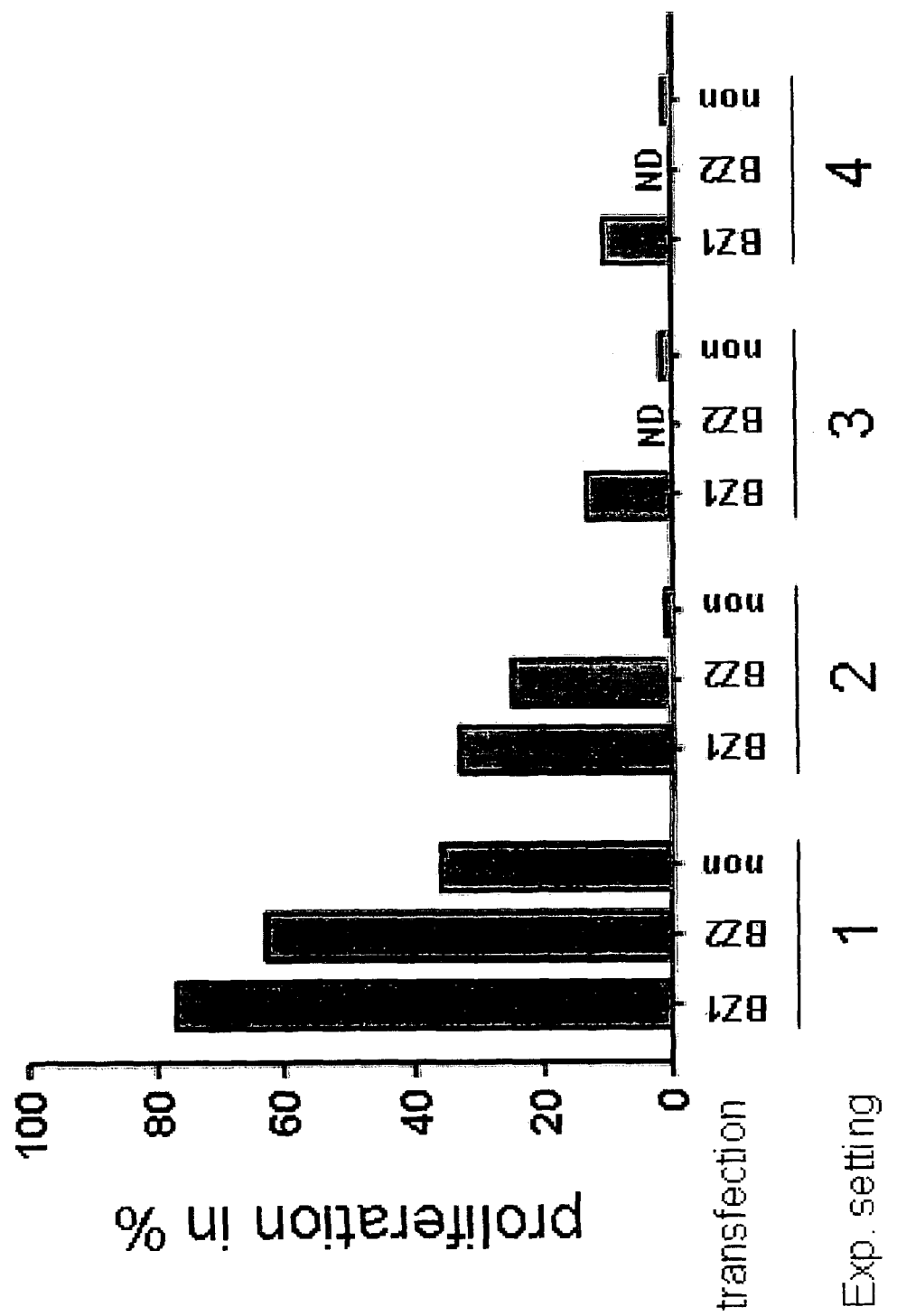

FIG. 7: Induction of proliferation in B cells expressing a recombinant protein of the present invention.

Mock transfected B cells and B cells transfected with IVT RNA encoding the recombinant proteins BZ1 and BZ2, respectively, were incubated with anti-CD40 (MAB89) (1), anti-c-myc (9E10) (2), irrelevant antibody (anti-CD3) (3), or pure medium (4). Proliferation was determined for viable (7-AAD$^-$, 7-Aminoactinomycin$^-$) CD20$^+$ B cells by measuring the reduction of CFSE staining intensity using flow cytometric analysis. ND=Not done.

Figure 8:
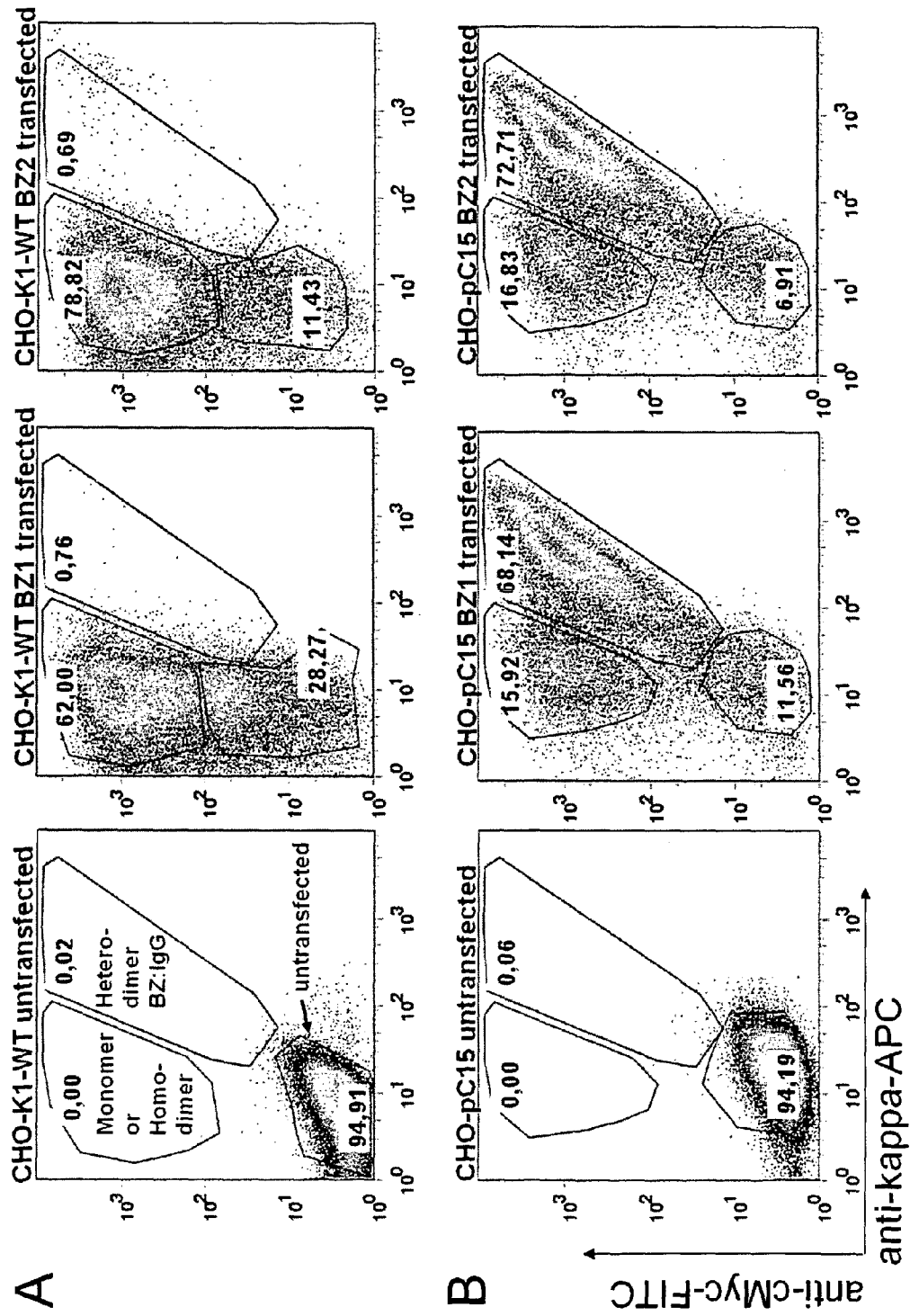

FIG. 8: Association of the recombinant protein of the present invention with immunoglobulin chains on the surface of cells analyzed by flow cytometry.

CHO-pC15 cells recombinantly expressing and secreting the light and heavy chain of a human monoclonal antibody and CHO-K1-WT cells have been transfected with IVT RNA encoding the recombinant proteins of the invention BZ1 and BZ2, respectively. As shown in panel (A), there is no anti-kappa detectable in CHO K1-WT cells under all conditions analyzed. Anti-kappa binds to the immunoglobulin light chain. However, a high expression of BZ1 and BZ2 is observed in BZ1- and BZ2-transfected CHO K1-WT cells, respectively, demonstrated by a strong c-myc staining. By contrast, IgG producing CHO-pC15 cells expressing BZ1 or BZ2 show a high percentage of kappa and c-myc double positive cells that is not detectable in untransfected cells (B). This population results from the interaction of the BZ proteins with IgG molecules on the surface of CHO-pC15 cells and shows the potential of the BZ1 and BZ2 constructs to form a heterodimer with an immunoglobulin chain derived from IgG.

Figure 9:
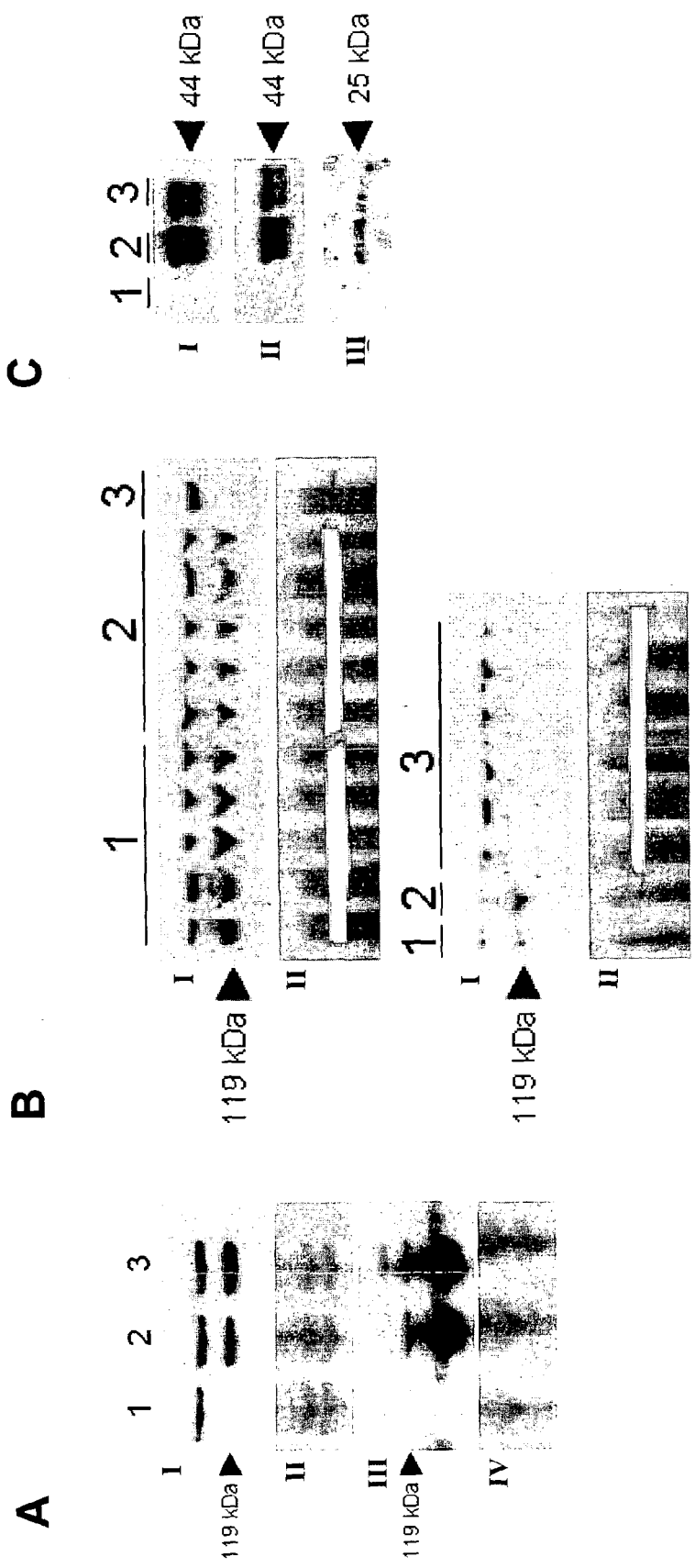

FIG. 9: Association of the recombinant protein of the present invention with immunoglobulin chains analyzed by Western blotting.

CHO-pC15 cells, which are CHO-K1 cells, genetically modified to constitutively produce the heavy and light chain of an immunoglobulin, were transfected with IVT RNA encoding the recombinant proteins of the present invention BZ1 and BZ2. (A) Cell lysates of untransfected (control), BZ1 and BZ2 transfected cells were loaded onto a gradient gel and separated via electrophoresis under non reducing conditions. 1: non transfected CHO-pC15; 2: BZ1 transfected CHO-pC15; 3: BZ2 transfected CHO-pC15; I: detected with anti-kappa antibody, II: representative Coomassie staining of PVDF membrane; III: detected with anti-c-myc antibodies, IV: representative Coomassie staining of PVDF membrane. The protein band of 119 kDa, which is not detectable in untransfected CHO cells, can be detected with anti-kappa and anti-c-myc antibodies. (B and C) The 119 kDa band obtained by electrophoresis under non reducing conditions was excised from the membranes, the proteins were eluted and separated again by SDS-PAGE under reducing conditions (C). The separated proteins have been detected with anti-CD40, anti-c-myc (both part of BZ proteins) and anti-kappa (immunoglobulin expressed by the CHO-pC15 cells) antibodies. It is demonstrated by the experiment depicted in FIG. 9 that BZ proteins are able to heterodimerize with endogenous immunoglobulin chains. (B) 1: BZ1 transfected CHO-pC15; 2: BZ2 transfected CHO-pC15; 3: non transfected CHO-pC15; I: detected with anti-kappa antibody, II: representative Coomassie stained and cut PVDF membranes. (C) 1: non transfected CHO-pC15; BZ1 transfected CHO-pC15; 3: BZ2 transfected CHO-pC15; I: detected with anti-CD40 antibody, II: detected with anti-c-myc antibody; III: detected with anti-kappa antibody.

Figure 10:
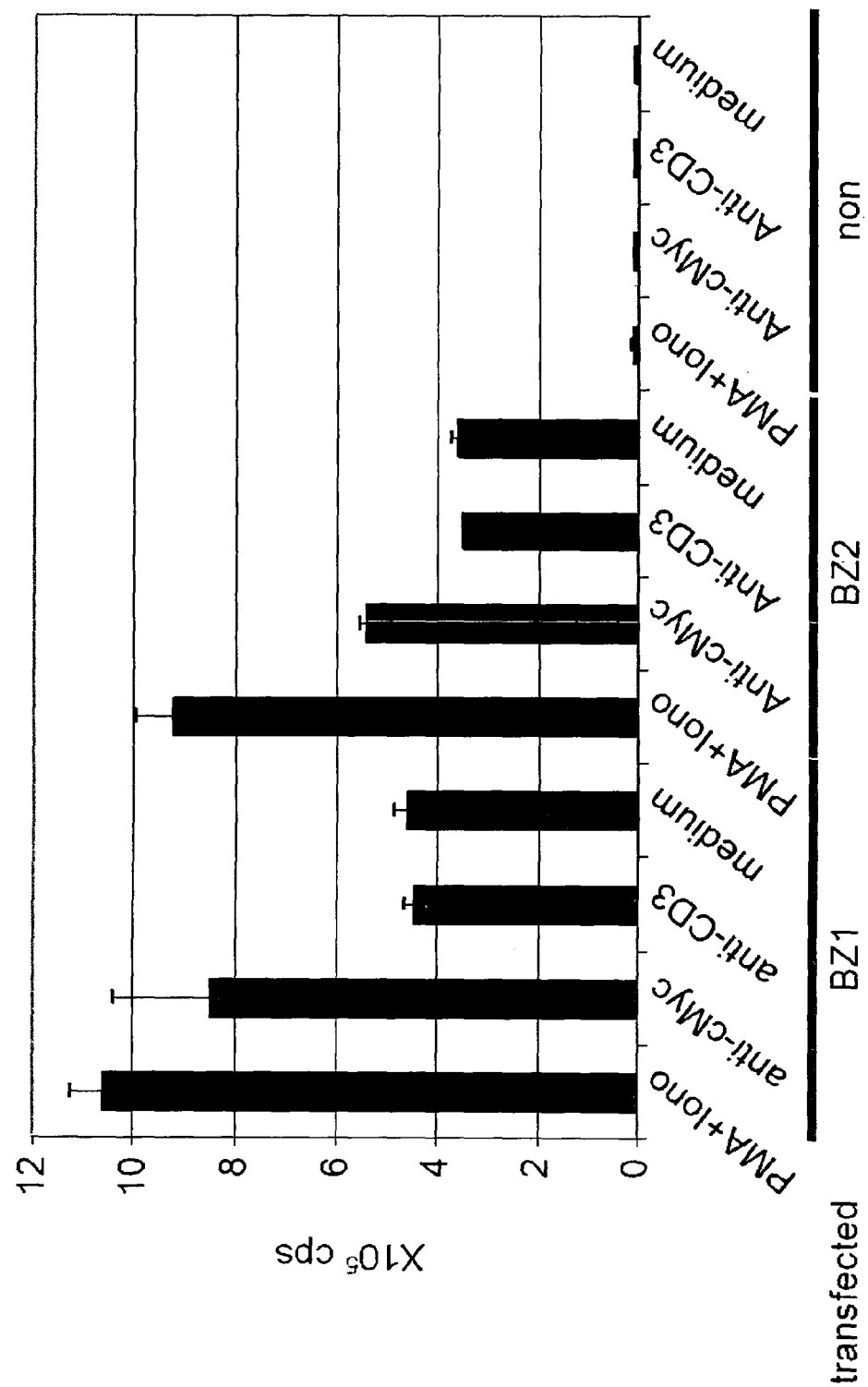

FIG. 10: NF-κB signaling in cells expressing a recombinant protein of the present invention.

HEK293 reporter cells stably transfected with a reporter plasmid including the luciferase gene under the control of an NF-κB-inducible ELAM1 composite promoter following transfection with RNA encoding the recombinant proteins BZ1 and BZ2, respectively, and incubation with an anti-cMyc antibody show activation of the NF-κB-inducible promoter demonstrating the functionality of the CD40 domain contained in the recombinant proteins BZ1 and BZ2, respectively.

Figure 11:
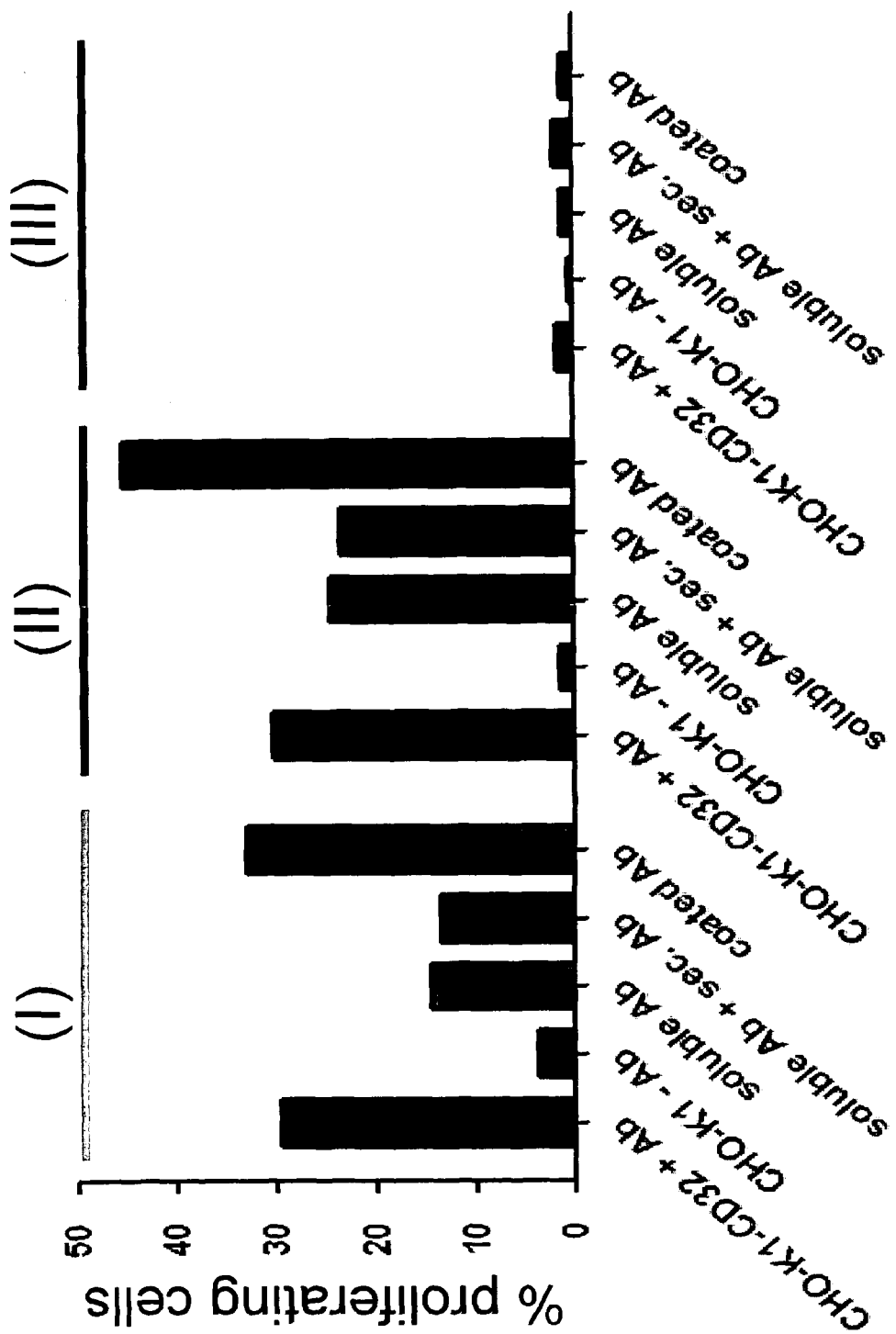

FIG. 11: Induction of proliferation of peripheral CD19$^+$ B cells expressing a recombinant protein of the present invention.

Proliferation of B cells transfected with RNA encoding the recombinant proteins BZ1 and BZ2, respectively, can be induced by a monoclonal antibody against cMyc (i) presented by a CD32 (Fc-gamma receptor) expressing cell line, (ii) in soluble form, (ii) cross-linked with a secondary anti-Fc antibody or (iii) coated on a culture dish.

Figure 12:
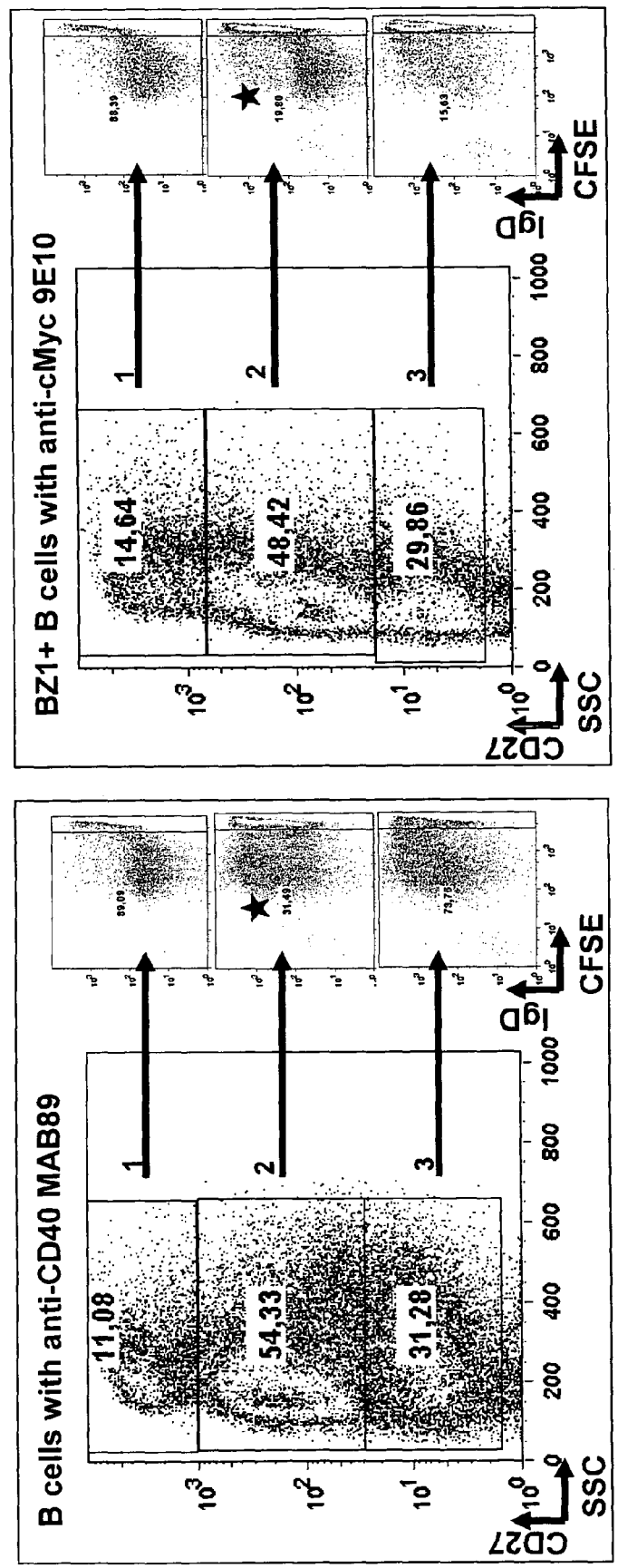

FIG. 12: Crosslinking of recombinant proteins of the present invention on the surface of CD19$^+$ B cells induces proliferation of class switched memory B cells.

CD19$^+$ B cells transfected with RNA encoding the recombinant protein BZ1 where activated using an anti-cMyc antibody. Non-transfected B cells were stimulated using an anti-CD40 MAB89 antibody. BZ stimulation predominantly activates IgG$^+$ B cells.

Figure 13:
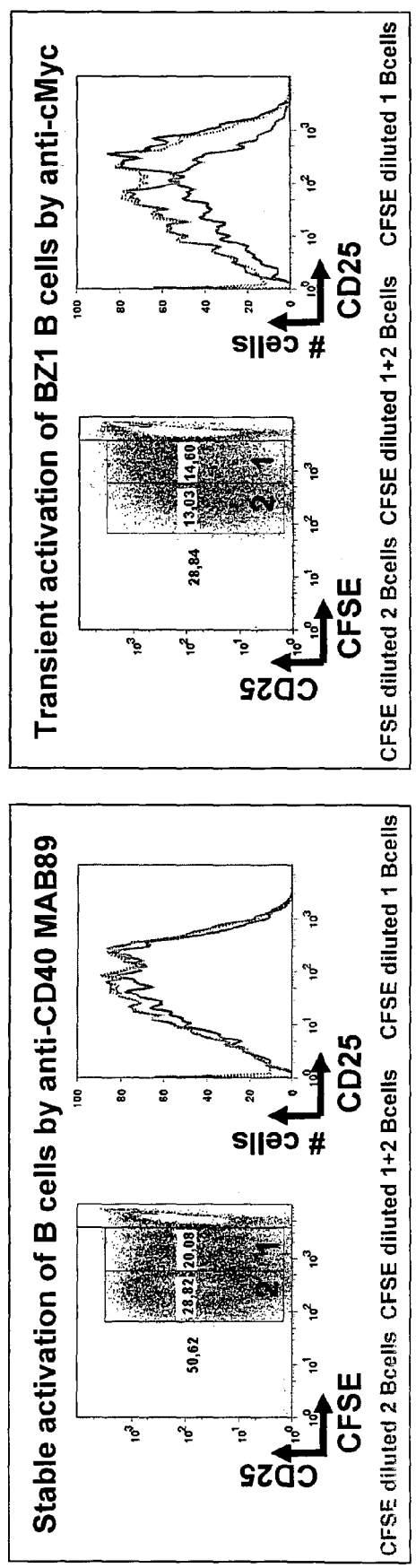

FIG. 13: Transient activation of B cells expressing a recombinant protein of the present invention.

Activation of peripheral B cells transfected with RNA encoding the recombinant protein BZ1 is reversible.

Figure 14:
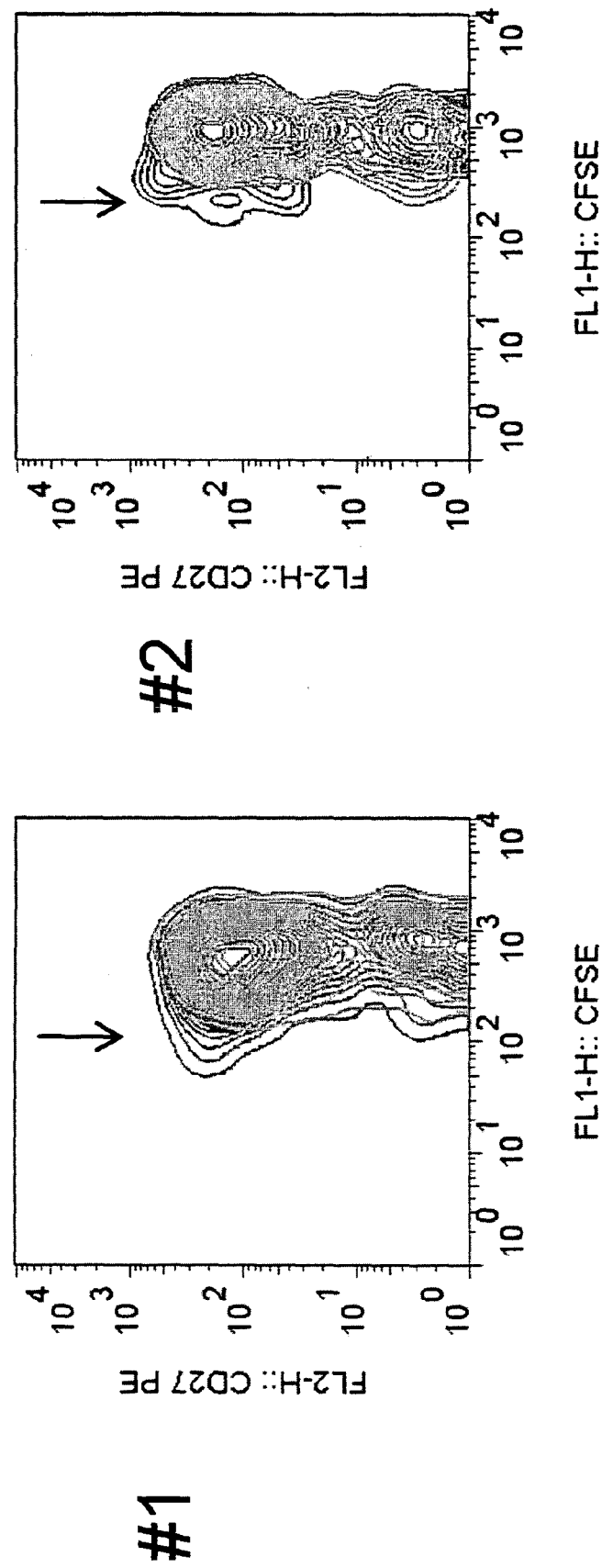

FIG. 14: Tetanus specific activation of IgG$^+$ memory B cells expressing a recombinant protein of the present invention The overlay of tetanus stimulated cells (red) and tetanus non-stimulated cells (blue) shows that tetanus specific IgG$^+$ memory B cells transfected with RNA encoding the recombinant protein BZ1 and stimulated with plate-coated tetanus toxoid show a higher proliferation rate compared to non-stimulated cells.

Figure 15:
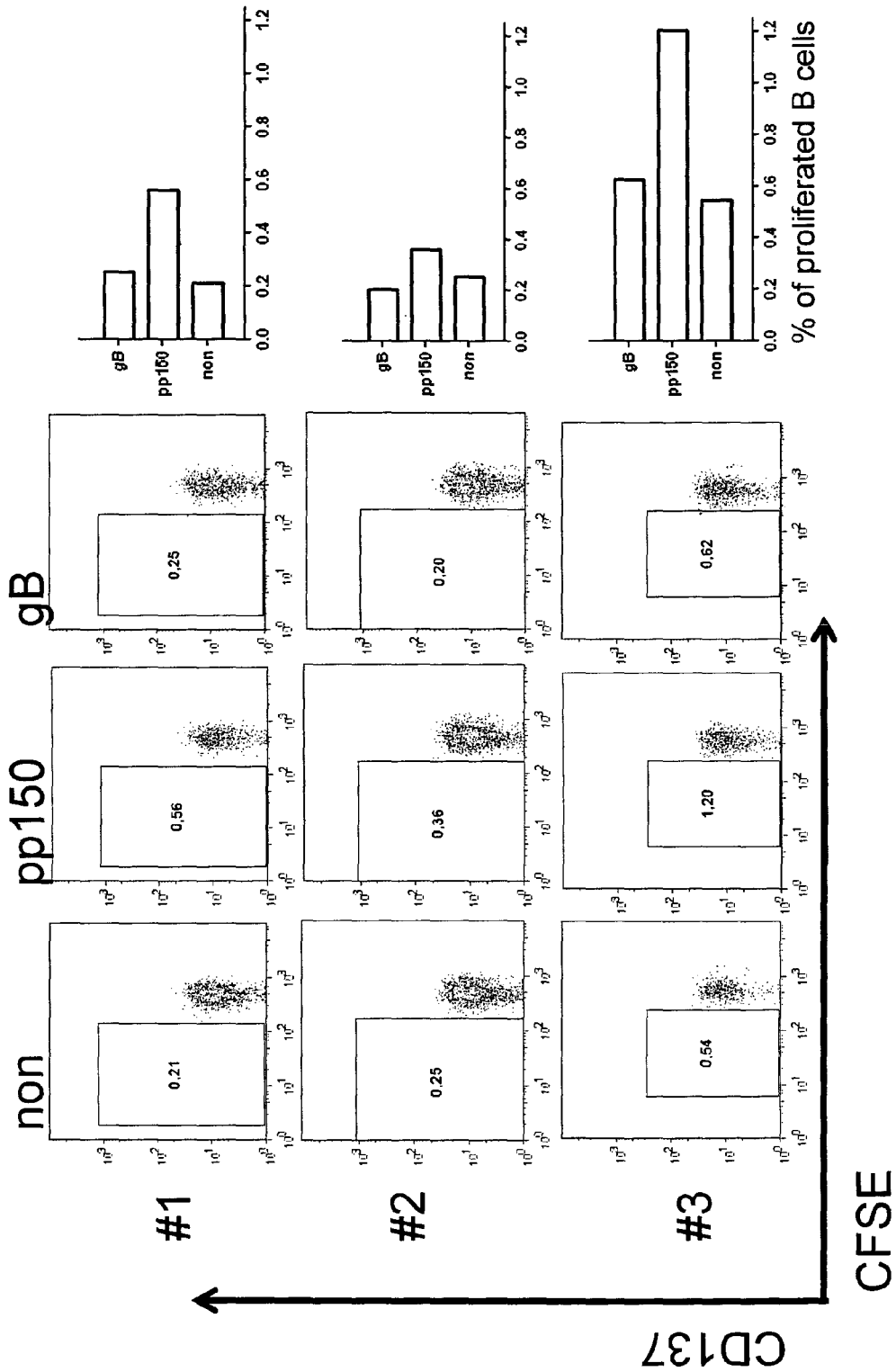

FIG. 15: CMV specific activation of IgG$^+$ memory B cells expressing a recombinant protein of the present invention CMV specific IgG$^+$ memory B cells from CMV infected patients transfected with RNA encoding the recombinant protein BZ1 and stimulated with plate-coated CMV protein pp150 or glycoprotein B (gB) show a higher proliferation rate compared to non-stimulated cells.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment of the recombinant protein of the present invention, the amino acid sequence mediating the association of the recombinant protein with the constant region of an immunoglobulin heavy chain comprises the $C_H2$ and the $C_H3$ region of an immunoglobulin and in another preferred embodiment, the transmembrane domain is the transmembrane domain of a BCR, it is a contemplated preferred embodiment of the recombinant protein of the present invention that the protein comprises the $C_H2$ and the $C_H3$ region of an immunoglobulin and the transmembrane domain of a BCR.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

In the following, definitions will be provided which apply to all aspects of the present invention.

The term "recombinant" in the context of the present invention means "made through genetic engineering". Preferably, a "recombinant entity" such as a recombinant protein in the context of the present invention is not occurring naturally, and preferably is a result of a combination of entities such as amino acid or nucleic acid sequences which are not combined in nature. For example, a recombinant protein in the context of the present invention may contain several amino acid sequences derived from different proteins fused together, e.g., by peptide bonds.

The term "CD40" refers to any, preferably naturally occurring, CD40 protein. CD40 is a transmembrane glycoprotein cell surface receptor that shares sequence homology with the tumor necrosis factor α (TNF-α) receptor family and was initially identified as a B cell surface molecule that induced B cell growth upon ligation with monoclonal antibodies. In the context of the present invention, CD40 may be derived from any species and is preferably human CD40. Preferably, human CD40 is a 277 amino acid protein that consists of a 193 amino acid extracellular domain including a 21 amino acid signal sequence, a 22 amino acid transmembrane domain, and a 62 amino acid cytoplasmic domain (van Kooten C. and Banchereau J., 2000, J. Leukoc. Biol. 67:2-17). Apart from B cells, CD40 expression has been shown for dendritic cells, macrophages, epithelial cells, hematopoietic progenitors, and activated T cells. Its ligand CD40L, also termed CD 154, is a 34-39 kDa type II integral membrane protein belonging to the TNF gene superfamily and is mainly expressed on activated T cells. Engagement of CD40 by its ligand leads to trimeric clustering of CD40 and the recruitment of adaptor proteins known as TNF receptor-associated factors (TRAFs) to the cytoplasmic tail of CD40. Binding of TRAFs results in formation of a signaling complex that includes multiple kinases and eventually leads to B cell clonal expansion, germinal center formation, isotype switching, affinity maturation, and generation of long-lived plasma cells (Quezeda S. A. et al., 2004, Annu. Rev. Immunol. 22:307-328).

The term "immunoglobulins" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "constant region of an immunoglobulin heavy chain" preferably refers to the region of the immunoglobulin heavy chain composed of the $C_H1$, $C_H2$, $C_H3$, and optionally the $C_H4$ domain, preferably comprising one or more, preferably all, potential linker and/or hinge regions. It is particularly preferred that the constant region of an immunoglobulin heavy chain comprises one or more cysteine residues which are capable of mediating the association with another constant region of an immunoglobulin heavy chain by disulfide-bonding.

The term "antibody" refers to a soluble immunoglobulin comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "amino acid sequence mediating the association of the recombinant protein with the constant region of an immunoglobulin heavy chain" preferably refers to any amino acid sequence that when folded in its proper three dimensional structure in the context of the recombinant protein of the present invention is capable of associating with any part of the constant region of an immunoglobulin heavy chain, for example with a part comprising one or more Ig domains, such as the $C_H1$, $C_H2$, $C_H3$, and the $C_H4$ domain. Thus, an amino acid sequence that when properly folded in the context of the recombinant protein of the present invention associates with the $C_H1$, $C_H2$, $C_H3$, and/or the $C_H4$ domain of an immunoglobulin heavy chain is encompassed by the above term. In this context, "association" means binding, wherein the binding may be covalent or non covalent. Preferably, association is covalent, for example, by the generation of disulfide bonds. In the context of the present invention, an amino acid sequence mediating the association of the recombinant protein of the present invention with the constant region of an immunoglobulin heavy chain is preferably a segment of an immunoglobulin constant region, preferably an immunoglobulin domain of an immunoglobulin constant region.

The term "B cell receptor" or "BCR" refers to the antigen receptor at the plasma membrane of B cells. The B cell receptor is generally composed of a surface bound IgM or IgD antibody associated with Ig-α and Ig-β heterodimers which are capable of signal transduction. The term "transmembrane domain of a B cell receptor" preferably refers to the transmembrane domain of the antibody part of the B cell receptor, i.e., the transmembrane domain of the IgM or IgD heavy chain. In the context of the present invention, the term "B cell receptor" or "BCR" preferably refers to a mature BCR and preferably excludes the pre-BCR which comprises a surrogate light chain.

The term "segment" refers to a part, preferably to a substantial part. The term "intracellular segment of CD40" refers to any intracellular part of a plasma membrane localized CD40, which is preferably capable of mediating the intracellular CD40 signal transduction. Said term may refer to the entire intracellular tail or intracellular domain of CD40 or to a portion thereof, wherein preferably said portion is capable of mediating the intracellular CD40 signal transduction. Preferably, said term refers to the entire intracellular tail of CD40.

The term "segment of an immunoglobulin constant region" refers to any part of an immunoglobulin constant region, preferably a part which is capable of folding into a three-dimensional structure, such as a domain. For example, a segment of an immunoglobulin constant region may be composed of one or more immunoglobulin domains of the constant region of an immunoglobulin chain, such as a $C_L$ domain of an immunoglobulin light chain or a $C_H1$, $C_H2$, $C_H3$, or $C_H4$ domain of the constant region of an immunoglobulin heavy chain, or a functionally equivalent part thereof. The term may also refer to more than one domain, for example, a segment of an immunoglobulin constant region may comprise, preferably consist of a $C_H1$ and a $C_H2$ domain, a $C_H2$ and a $C_H3$ domain, or a $C_H3$ and a $C_H4$ domain of an immunoglobulin heavy chain, such as an α, δ, ε, γ, or μ immunoglobulin heavy chain. It may also comprise, preferably consist of three or four domains or two or more domains that are not normally connected in an immunoglobulin chain, such as a $C_H1$ and a $C_H3$ domain. In the context of the present invention, a "segment of an immunoglobulin constant region" preferably comprises at least one cysteine that is capable of generating a disulfide bond with a cysteine located within the constant region of an immunoglobulin heavy chain, for example, within the $C_H1$, $C_H2$, $C_H3$, or $C_H4$ domain or any linker region or hinge region within the constant region of an immunoglobulin heavy chain. In the context of the present invention, a segment of an immunoglobulin constant region which comprises, preferably consisting of a $C_H2$ and a $C_H3$ domain also comprises an optional linker or hinge region which may be normally present between a $C_H1$ and a $C_H2$ domain.

The term "part" refers to a continuous element. For example, a part of a structure such as an amino acid sequence or protein refers to a continuous element of said structure. A portion or a part of a structure preferably comprises one or more functional properties of said structure. For example, a portion or a part of a protein or peptide is preferably functionally equivalent to the protein or peptide it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

The term "capable of mediating the intracellular CD40 signal transduction" means capable of initiating signaling events that are usually initiated by the intracellular region of CD40 if the extracellular region of CD40 is engaged with its ligand, i.e., CD40L. Such signaling events include, for example, the recruitment of signaling and/or adaptor proteins or molecules such as the TNF receptor-associated factors (TRAFs) to the CD40 cytoplasmic tail and the formation of a signaling complex that includes multiple kinases such as the NF-κB inducing kinase (NIK), receptor-interacting protein (RIP), and members of the mitogen-activated protein kinase (MAPK) family. Clustering of these kinases then initiates a downstream cascade of signaling events, finally resulting in the transcription of target genes (cf., e.g., Quezeda S. A. et al., 2004, supra). CD40 signaling in a B cell in the presence of cytokines can induce proliferation, clonal expansion, and differentiation to Ig secretion. In the context of the present invention, an entity such as an intracellular segment of CD40 or a variant thereof is capable of mediating the intracellular CD40 signal transduction, if in the context of a CD40 molecule said intracellular segment or variant thereof results in the same signal transduction events as the wild type CD40 molecule when exposed to the appropriate stimuli, such as CD40L binding to the CD40 extracellular domain.

For the purposes of the present invention, "variants" of a protein or peptide or of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence, e.g., between the preferred intracellular segment of CD40 set forth in SEQ ID NO: 1 and the variant the intracellular segment of CD40, will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

The above definition for protein variants, i.e., amino acid sequence variants, also applies correspondingly to nucleic acid sequence variants.

The protein and nucleic acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

According to the invention, a variant, portion, or part of a peptide or protein or of a nucleic acid or amino acid sequence preferably has a functional property of the peptide or protein or the nucleic acid or amino acid sequence, respectively, from which it has been derived. Such functional properties comprise the interaction with other peptides or proteins or the capability of exerting signaling function. In other words, a variant, portion, or part of a peptide or protein or of a nucleic acid or amino acid sequence preferably is functionally equivalent to the peptide or protein or the nucleic acid or amino acid sequence, respectively, from which it has been derived.

The term "functionally equivalent" means being capable of exerting the same or essentially the same function with respect to one or more functional properties such as signal transduction properties or binding to other proteins or peptides. In the context of the recombinant protein of the present invention "functionally equivalent" preferably means that the functionally equivalent protein is capable of mediating the intracellular CD40 signal transduction and is capable of associating with the constant region of an immunoglobulin chain. Preferably, said functionally equivalent protein is capable of forming a complex with an immunoglobulin chain when expressed in a cell that also expresses immunoglobulin chains, and preferably said complex is able to localize to the plasma membrane of said cell.

Residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (www.ebi-.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Residues in two or more polypeptide sequences are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20, or 30 amino acids.

In the context of the present invention, amino acid sequences are meant to be "linked" if they are coupled to each other, preferably via peptide bonds. Amino acid sequences are meant to be linked via another amino acid if the latter couples said amino acids, preferably via peptide bonds.

The terms "domain" or "region" relate to a particular part of an amino acid sequence which can preferably be connected to a specific function or structure. Preferably, a "domain" of a protein refers to a part of the protein which can fold into a stable three-dimensional structure and which is preferably stable and folded even when separated from the entire protein it is derived from. For example, the immunoglobulin heavy chains contain a constant region and a variable region. The constant region comprises several domains, for example, the $C_H1$, $C_H2$, $C_H3$, and optionally the $C_H4$ domain.

The term "transmembrane domain" or "transmembrane region" relates to the part of a protein which essentially accounts for the portion present in a cellular membrane and preferably serves to anchor the protein in the membrane. A transmembrane domain is preferably according to the invention an amino acid sequence which spans the membrane once. However, it is also possible in certain embodiments to use a transmembrane domain which spans the membrane more than once. The transmembrane domain will generally have 15-25 preferably hydrophobic uncharged amino acids which assume for example an α-helical conformation (cf., e.g., Singer S.J., 1990, Annu. Rev. Cell Biol. 6:247-296). Typical transmembrane domains that can be used in the context of the present invention may be selected, e.g., from the Protein Data Bank of Transmembrane Proteins (pdbtm.enzim.hu/?). The transmembrane domain in the context of the present invention is preferably derived from a protein selected from the group consisting of a B cell receptor and CD40. In preferred embodiments, the transmembrane domain is derived from the CD40 transmembrane domain (ALVVIPIIFGILFAILLV-LVFI; SEQ ID NO: 4) or is derived from a transmembrane domain of a BCR (for example, ITIFITLFLLSVCY-SATVTFF; SEQ ID NO: 3, preferably GELDGLWTTITI-FITLFLLSVCYSATVTFF; SEQ ID NO: 9). The transmembrane domain allows the recombinant protein of the present invention to span the membrane.

The term "derived" means according to the invention that a particular entity, in particular a particular sequence, is present in the object from which it is derived, in particular an organism or molecule. In the case of nucleic acid and amino acid sequences, especially particular sequence regions, "derived" additionally means that the relevant nucleic acid or amino acid sequence is derived from a nucleic acid or amino acid sequence which is present in the object. Thus, the expression "a transmembrane domain derived from a BCR" means that said transmembrane domain is present in the BCR. A sequence derived from an amino acid or a nucleic acid sequence may relate according to the invention to homologous sequences and derivatives of the former sequence.

Homologous amino acid sequences exhibit according to the invention at least 40%, in particular at least 50%, at least 60%, at least 70%, at least 80%, at least 90% and preferably at least 95%, at least 98 or at least 99% identity of the amino acid or nucleic acid residues.

"Derivatives" of a protein or polypeptide or of an amino acid sequence in the sense of this invention include amino acid insertion variants, amino acid deletion variants and/or amino acid substitution variants. "Derivatives" of proteins or polypeptides also include according to the invention single or multiple substitutions, deletions and/or additions of any molecules which are associated with the protein or polypeptide, such as carbohydrates, lipids and/or proteins or polypeptides. In one embodiment, "derivatives" of proteins or polypeptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. Derivatives of proteins or polypeptides may also be prepared by other methods such as, for example, by chemical cleavage with cyanogen bromide, trypsin, chymotrypsin, papain, V8 protease, $NaBH_2$, acetylation, formylation, oxidation, reduction or by metabolic synthesis in the presence of tunicamycin. The term "derivative" also extends to all functional chemical equivalents of proteins or polypeptides. The derivatives, described above, of proteins and polypeptides are encompassed according to the invention by the term "fusion molecule", even if no express reference is made thereto.

The term "marker region" refers to a region which contains a label. Preferably, said label is useful for identifying or detecting the entity which comprises the marker region. The label may be any entity that is useful for being detected, such as a fluorescent label, a radioactive label, or an epitope tag. Preferably the marker region comprises one or more epitope tags. An amino acid sequence comprising a marker region preferably means an amino acid sequence comprising one or more peptide or protein tags, e.g., epitope tags such as myc-tags, HA-tags, FLAG-tags, T7-tags, S-tags, GST-tag, and/or His-tags, or fluorescent protein tags, such as GFP-, EGFP-, YFP-, EYFP-, CFP-, ECFP-, DsRed-, or mRFP-tags. A peptide or protein tag may be detected by antibodies directed to said tag. An amino acid sequence comprising a marker region may also refer to an amino acid sequence which comprises one or more labeled amino acids such as radioactive amino acids, biotin labeled amino acids, or fluorescently labeled amino acids.

A nucleic acid is according to the invention preferably deoxyribonucleic acid (DNA) or ribonucleic acid (RNA), more preferably RNA, most preferably in vitro transcribed RNA (IVT RNA). Nucleic acids include according to the invention genomic DNA, cDNA, mRNA, recombinantly prepared and chemically synthesized molecules. A nucleic acid may according to the invention be in the form of a molecule which is single stranded or double stranded and linear or closed covalently to form a circle. A polynucleotide according to the invention preferably comprises a nucleic acid sequence encoding the recombinant protein of the present invention. The polynucleotide of the invention can be employed for transfection of host cells, for example, in the form of RNA which can be prepared by in vitro transcription from a DNA template. The RNA can moreover be modified before application by stabilizing sequences, capping, and polyadenylation.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention may be obtained by in vitro transcription of an appropriate DNA template. The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA.

The term "expression" is used herein in its broadest meaning and comprises the production of RNA or of RNA and protein. With respect to RNA, the term "expression" or "translation" relates in particular to the production of peptides or proteins. Expression may be transient or may be stable.

The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

The term "host cell" relates according to the invention to any cell which can be transformed or transfected with an exogenous nucleic acid, e.g., with a polynucleotide comprising a nucleic acid sequence encoding the recombinant protein of the present invention. The term "host cells" includes according to the invention prokaryotic (e.g., *E. coli*) or eukaryotic (e.g., dendritic cells, B cells, CHO cells, COS cells, K562 cells, HEK293 cells, HELA cells, yeast cells, and insect cells). The exogenous nucleic acid may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or a vector of the invention. The term "host cell" includes the progeny of the original cell which has been transformed, transfected, or infected with exogenous nucleic acids, e.g., the polynucleotide or the vector of the invention. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the host cell is an antigen-presenting cell, in particular a dendritic cell, a monocyte, or macrophage. A nucleic acid sequence encoding the recombinant protein of the present invention may be present in the host cell in a single or in multiple copies and is, in one embodiment, expressed in the host cell. In particular preferred embodiments, the host cells according to the present invention are B cells, preferably human B cells.

The term "transfection" relates to the introduction of nucleic acids such as the polynucleotide of the invention into a host cell. The person skilled in the art is well aware of methods for introducing polynucleotides or vectors into host cell. Cells can be transfected, for example, using commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), protein-mediated transfection, magnet-assisted transfection, optical transfection, electroporation, or viral infection. In the context of the present invention, a particularly preferred transfection method is electroporation, preferably electroporation of RNA, preferably IVT RNA.

The term "B cell" refers to a B lymphocyte. B cell precursors reside in the bone marrow where immature B cells are produced. B cell development occurs through several stages, each stage representing a change in the genome content at the antibody loci. In the genomic heavy chain variable region there are three segments, V, D, and J, which recombine randomly, in a process called VDJ rearrangement to produce a unique variable region in the immunoglobulin of each B cell. Similar rearrangements occur for the light chain variable region except that there are only two segments involved, V and J. After complete rearrangement, the B cell reaches the IgM$^+$ immature stage in the bone marrow. These immature B cells present a membrane bound IgM, i.e., BCR, on their surface and migrate to the spleen, where they are called transitional B cells. Some of these cells differentiate into mature B lymphocytes. Mature B cells expressing the BCR on their surface circulate the blood and lymphatic system performing the role of immune surveillance. They do not produce soluble antibodies until they become fully activated. Each B cell has a unique receptor protein that will bind to one particular antigen. Once a B cell encounters its antigen and receives an additional signal from a T helper cell, it can further differentiate into either a plasma B cell expressing and secreting soluble antibodies or a memory B cell.

In the context of the present invention, the term "B cell" preferably refers to any B lymphocyte which presents a fully rearranged, i.e., a mature, BCR on its surface. For example, a B cell in the context of the present invention may be an immature or a mature B cell and is preferably a naïve B cell, i.e., a B cell that has not been exposed to the antigen specifically recognized by the BCR on the surface of said B cell. In preferred embodiments, the B cells are CD19$^+$ B-cells, i.e., express CD19 on their surface. It is particularly preferred that the B cells in the context of the present invention are CD19$^+$ B cells and express a fully rearranged BCR on their surface. The B cells may also be CD20$^+$ or CD21$^+$ B cells which preferably carry a BCR on their surface. In preferred embodiments, the B cells are memory B cells, preferably IgG$^+$ memory B cells. The term "B cells" in the context of the present invention preferably refers to a mixture of B cells. A mixture of B cells preferably means that the B cells in the mixture have different antigen-specificities, i.e., produce antibodies or fully rearranged BCRs which recognize a variety of antigens. The antibodies or BCRs of a single B cell are usually identical, also with respect to antigen-specificity.

The term "B cells secreting antibodies" preferably refers to plasma B cells. The term "B cells carrying a BCR on their surface" preferably refers to B cells expressing a BCR, preferably a fully rearranged BCR, at their plasma membrane. In this context, "a BCR" preferably does not mean a single BCR but preferably means a multitude of BCRs having the same antigen-specificity. The term "proliferating B cells" preferably refers to dividing B cells. Proliferating B cells may, for example, be identified by labeling with CFSE and measuring the CFSE fluorescence intensity, for example, using flow cytometry as described herein in the Examples section.

The term "B cell repertoire of a subject" as used herein refers to the entirety of the B cell population in a subject. Preferably, said term is used with respect to antigen-specificity. Thus, preferably, the term "B cell repertoire of a subject" in the context of the present invention refers to a mixture of B cells of said subject comprising at least one B cell of each B cell antigen-specificity present in said subject. The term "B cell antigen-specificity" refers to the antigen-specificity of the antibodies or fully rearranged BCR expressed by said B cell.

The term "portion" refers to a fraction. A portion preferably means at least 20%, at least 30%, preferably at least 40%, preferably at least 50%, more preferably at least 60%, more preferably at least 70%, even more preferably at least 80%, and most preferably at least 90% of the entire entity. The term "substantial portion" preferably refers to at least 50%, more preferably at least 60%, more preferably at least 70%, even more preferably at least 80%, even more preferably at least 90%, even more preferably at least 95%, and most preferably at least 99% of the entire entity.

The terms "subject" and "individual" are used interchangeably and preferably relate to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease.

The term "clonal expansion" refers to a process wherein a specific entity is multiplied. In the context of the present invention, the term is preferably used in the context of an immunological response in which lymphocytes, preferably B lymphocytes, are stimulated by an antigen, proliferate, and the specific lymphocyte recognizing said antigen is amplified. Preferably, clonal expansion leads to differentiation of the lymphocytes, preferably into lymphocytes producing and secreting antibodies. B lymphocytes secreting antibodies are, for example, plasma B cells.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes derivatized antigens as secondary substance which becomes antigenic— and sensitizing—only through transformation (e.g., intermediately in the molecule, by completion with body protein), and conjugated antigens which, through artificial incorporation of atomic groups (e.g., isocyanates, diazonium salts), display a new constitutive specificity. In a preferred embodiment, the antigen is a tumor antigen, i.e., a constituent of cancer cells which may be derived from the cytoplasm, the cell surface and the cell nucleus, in particular those antigens which are produced, preferably in large quantity, intracellularly or as surface antigens on tumor cells. Examples are carcinoembryonic antigen, $\alpha$1-fetoprotein, isoferritin and fetal sulfoglycoprotein, $\alpha$2-H-ferroprotein and $\gamma$-fetoprotein and various viral tumor antigens. In a further embodiment, the antigen is a viral antigen such as viral ribonucleoproteins or envelope proteins. In particular, the antigen or peptides thereof should be recognizable by a B cell receptor or an immunoglobulin molecule such as an antibody.

Preferably, the antigen if recognized by a B cell receptor is able to induce in presence of appropriate co-stimulatory signals, clonal expansion of the B cell carrying the BCR specifically recognizing the antigen and the differentiation of such B cells into antibody secreting B cells. In preferred embodiments of the present invention, an antigen is present in a repetitive organization, i.e., the antigen comprises more than one, preferably at least 2, at least 3, at least 4, up to 6, 10, 12 or more agents or epitopes against which an immune response is to be generated or against which the antibodies which are to be produced according to the present invention are to be directed. Such repetitive antigen preferably is capable of binding to more than one antibody of the same specificity. In other words, such repetitive antigen comprises more than one epitope, preferably identical epitope, and thus is capable of "crosslinking" antibodies directed to said epitope. The more than one agents or epitopes may be covalently or non-covalently linked, wherein a covalent linkage may be by any chemical grouping such as by peptide linkages. In one preferred embodiment, an antigen is a fusion molecule comprising a repetition of an antigen peptide or comprising different antigen peptides having a common epitope. In one preferred embodiment, said antigen peptides are linked by peptide linkers.

The term "self tolerance" designates a mechanism, where the body does not mount an immune response to self proteins. Normally, self-tolerance is developed early by developmental events within the immune system that prevent, in particular, the organism's own T cells and B cells from reacting with the organism's own tissues.

An "autoantibody" is an antibody that reacts with the cells, tissues, or native proteins of the individual in which it is produced, i.e., which reacts with self-proteins of said individual.

DETAILED DESCRIPTION

In a first aspect, the present invention provides a recombinant protein comprising:
(a) the amino acid sequence of an intracellular segment of CD40 or of a variant thereof which is capable of mediating the intracellular CD40 signal transduction and
(b) an amino acid sequence mediating the association of the recombinant protein with the constant region of an immunoglobulin heavy chain,
wherein the amino acid sequences under (a) and (b) are linked via
(c) an amino acid sequence comprising the amino acid sequence of a transmembrane domain.

The amino acid sequence mediating the association of the recombinant protein with the constant region of an immunoglobulin heavy chain may mediate the association with any immunoglobulin heavy chain, such as an immunoglobulin α, δ, ε, γ, or μ heavy chain or any possible subtypes thereof, such as α1, α2, γ1, γ2, γ3, γ4 etc.

In a preferred embodiment, the amino acid sequence mediating the association of the recombinant protein with the constant region of an immunoglobulin heavy chain comprises the amino acid sequence of a segment of an immunoglobulin constant region. For example, the amino acid sequence mediating the association of the recombinant protein with the constant region of an immunoglobulin heavy chain may comprise a segment of an immunoglobulin constant region derived from an immunoglobulin α, δ, ε, γ, or μ heavy chain, such as an immunoglobulin α1, α2, γ1, γ2, γ3, or γ4 chain, or from an immunoglobulin lambda or kappa light chain, preferably from an immunoglobulin α, δ, ε, γ, or μ heavy chain. Preferably, said segment of an immunoglobulin constant region comprises a cysteine residue that is capable of forming a disulfide bond with a cysteine residue within the constant region of an immunoglobulin heavy chain, for example, of an immunoglobulin α, δ, ε, γ, or μ heavy chain.

In preferred embodiments, the segment of an immunoglobulin constant region preferably comprised by the recombinant protein of the present invention and the constant region of an immunoglobulin heavy chain with which the association is mediated are matched. This means that if the immunoglobulin heavy chain with which the amino acid sequence mediating the association of the recombinant protein with the constant region of an immunoglobulin heavy chain is an immunoglobulin γ heavy chain, the segment of an immunoglobulin constant region is preferably derived from an immunoglobulin γ heavy chain, if the immunoglobulin heavy chain with which the amino acid sequence mediating the association of the recombinant protein with the constant region of an immunoglobulin heavy chain is an immunoglobulin α heavy chain, the segment of an immunoglobulin constant region is preferably derived from an immunoglobulin α heavy chain, if the immunoglobulin heavy chain with which the amino acid sequence mediating the association of the recombinant protein with the constant region of an immunoglobulin heavy chain is an immunoglobulin δ heavy chain, the segment of an immunoglobulin constant region is preferably derived from an immunoglobulin δ heavy chain, if the immunoglobulin heavy chain with which the amino acid sequence mediating the association of the recombinant protein with the constant region of an immunoglobulin heavy chain is an immunoglobulin ε heavy chain, the segment of an immunoglobulin constant region is preferably derived from an immunoglobulin ε heavy chain, and if the immunoglobulin heavy chain with which the amino acid sequence mediating the association of the recombinant protein with the constant region of an immunoglobulin heavy chain is an immunoglobulin μ heavy chain, the segment of an immunoglobulin constant region is preferably derived from an immunoglobulin μ heavy chain. Preferably, also the subtypes are matched. Preferably, also the particular $C_H$ domains are matched. It is particularly preferred, that the segment of an immunoglobulin constant region is chosen such that it is essentially identical to a part of the constant region of the immunoglobulin heavy chain with which the association is mediated, preferably such that the association is comparable to the association between two normally associating heavy chains.

Preferably, the amino acid sequence mediating the association of the recombinant protein with the constant region of an immunoglobulin heavy chain comprises one or more immunoglobulin domains of the constant region of an immunoglobulin chain, such as one or more of the $C_H1$, $C_H2$, $C_H3$, or the $C_H4$ domain, for example, the $C_H1$ and the $C_H2$ domain, the $C_H2$ and the $C_H3$ domain, the $C_H3$ and the $C_H4$ domain, preferably the $C_H2$ region or the $C_H2$ and the $C_H3$ region of an immunoglobulin heavy chain, for example, of an immunoglobulin α, δ, ε, γ, or μ heavy chain, preferably of an immunoglobulin γ heavy chain, more preferably of the immunoglobulin γ1 heavy chain, i.e., of IgG1. For example, the amino acid sequence mediating the association of the recombinant protein with the constant region of an immunoglobulin heavy chain, preferably the segment of an immunoglobulin constant region, preferably the one or more $C_H$ domains may be derived from an IgM antibody heavy chain such as the IgM antibody heavy chain set forth in the GenBank data base entry under accession number AAS01770.1 (SEQ ID NO: 12), from an IgD antibody heavy chain such as the IgD antibody heavy chain set forth in the GenBank data base entry under accession number AAB21246.1 (SEQ ID NO: 13), from an IgG2 antibody heavy chain such as the IgG2 antibody heavy chain set forth in the GenBank data base entry under accession number AAR26706.1 (SEQ ID NO: 14), from an IgG3 antibody heavy chain such as the IgG3 antibody heavy chain set forth in the GenBank data base entry under accession number AAG00911.1 (SEQ ID NO: 15), from an IgG4 antibody heavy chain such as the IgG4 antibody heavy chain set forth in the GenBank data base entry under accession number AAG00912.1 (SEQ ID NO: 16), from an IgE antibody heavy chain such as the IgE antibody heavy chain set forth in the GenBank data base entry under accession number AAB59424.1 (SEQ ID NO: 17), or from an IgA antibody heavy chain such as the IgA antibody heavy chain set forth in the GenBank data base entry under accession number AAT74070.1 (SEQ ID NO: 18).

Preferably, the amino acid sequence mediating the association of the recombinant protein with the constant region of an immunoglobulin heavy chain is derived from, preferably comprises, preferably essentially consists of, preferably consists of an amino acid sequence selected from the group consisting of:

(I) the amino acid sequence set forth in SEQ ID NO: 2 and 19 or a part thereof, and
(II) an amino acid sequence which is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the amino acid sequence or the part thereof under (I), preferably over the entire length of the amino acid sequence or the part thereof.

In a preferred embodiment, the amino acid sequence of an intracellular segment of CD40 or of a variant thereof is derived from, preferably comprises, preferably essentially consists of, preferably consists of an amino acid sequence selected from the group consisting of:

(I) the amino acid sequence set forth in SEQ ID NO: 1 or a part thereof which is capable of mediating the intracellular CD40 signal transduction, and
(II) an amino acid sequence that is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the amino acid sequence or the part thereof under (I), preferably over the entire length of the amino acid sequence or the part thereof, and is capable of mediating the intracellular CD40 signal transduction.

In a preferred embodiment, the order of the elements comprised by the recombinant protein of the present invention is, from the amino-terminus to the carboxy-terminus, the amino acid sequence mediating the association of the recombinant protein with the constant region of an immunoglobulin heavy chain, the amino acid sequence comprising the amino acid sequence of a transmembrane domain, and the amino acid sequence of an intracellular segment of CD40 or of a variant thereof which is capable of mediating the intracellular CD40 signal transduction. Preferably, the carboxy-terminal end of (b) the amino acid sequence mediating the association of the recombinant protein with the constant region of an immunoglobulin heavy chain is linked to the amino-terminal end of (a) the amino acid sequence of an intracellular segment of CD40 or of a variant thereof which is capable of mediating the intracellular CD40 signal transduction. Preferably, said amino acid sequences are linked through an amino acid sequence comprising the amino acid sequence of a transmembrane domain.

In one embodiment, the recombinant protein of the present invention further comprises an amino acid sequence comprising a marker region. The amino acid sequence comprising a marker region may be located anywhere within the recombinant protein of the present application, for example, it may be localized N-terminally or C-terminally, preferably directly N-terminally or C-terminally, of any of the elements comprised by the recombinant protein of the present invention, e.g., N-terminally or C-terminally of the intracellular segment of CD40 or a variant thereof, N-terminally or C-terminally of the transmembrane domain, or N-terminally or C-terminally of the amino acid sequence mediating the association of the recombinant protein with the constant region of an immunoglobulin heavy chain. The amino acid sequence comprising a marker region may also be localized within each of the elements comprised by the recombinant protein of the invention. Preferably, the amino acid sequence comprising a marker region is fused to the amino-terminal end of (b) the amino acid sequence mediating the association of the recombinant protein with the constant region of an immunoglobulin heavy chain. The marker region may comprise any label as described above, such as a fluorescent label, a radioactive label, or an epitope tag, and preferably comprises one or more amino acid sequences of an epitope tag selected from the group consisting of HA-tag, myc-tag, FLAG-tag, His-tag. A preferred combination of epitope tags within the marker region in the context of the present invention is the combination of a myc-tag, such as a c-myc-tag, and a hemagglutinin tag (HA-tag), preferably in the combination myc-HA-myc. However, it is to be understood that any combination of epitope tags is contemplated. The marker region may serve to detect the recombinant protein of interest. For example, if a polynucleotide comprising a nucleic acid sequence encoding the recombinant protein of the present invention which comprises a marker region is transfected into cells, the expression of said polynucleotide can be monitored by detecting, for example, the epitope-tag within the marker region. Preferably, the marker region is not essential for the function of the recombinant protein with respect to induction of clonal expansion of B cells or the production of B cells secreting antigen-specific antibodies.

The transmembrane domain in the context of the present invention may be any transmembrane domain as described above, preferably the transmembrane domain spans the membrane an odd number of times, such as once, three times, five times, or seven times, preferably only once. Thus, it is preferred that two amino acid sequences attached to the amino-terminal and the carboxy-terminal end of the transmembrane domain, respectively, are positioned on opposite sides of the membrane which is crossed by the transmembrane domain. In a preferred embodiment, the transmembrane domain is derived from a member of the immunoglobulin superfamily, like B cell receptor (BCR), IgM, semaphorine 4D, selectine, integrine, or ICAM (inter-cellular adhesion molecule), or from a member of the tumor necrosis factor receptor (TNFR) superfamily, like CD40, CD120, Lymphotoxin β receptor, CD134, FAS, TNFRSF6B, CD27, CD30, CD137, RANK, Osteoprotegerin, TNFRSF25, or Ectodysplasin A2 receptor. Preferably, the transmembrane domain is derived from a transmembrane domain selected from the group consisting of the transmembrane domain of a B cell receptor (BCR) and the transmembrane domain of CD40, preferably the transmembrane domain is selected from the group consisting of the transmembrane domain of a B cell receptor (BCR) and the transmembrane domain of CD40. Preferably, the amino acid sequence of a transmembrane domain is derived from, preferably comprises, preferably essentially consists of, preferably consists of an amino acid sequence selected from the group consisting of:

(I) the amino acid sequences set forth in SEQ ID NOs: 3, 4, and 9 or a part thereof, and (II) an amino acid sequence which is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the amino acid sequence or the part thereof under (I), preferably over the entire length of the amino acid sequence or the part thereof.

In a preferred embodiment, the recombinant protein of the present invention is derived from, preferably comprises, preferably essentially consists of, preferably consists of an amino acid sequence selected from the group consisting of:

(I) the amino acid sequences set forth in SEQ ID NOs: 5 and 6, or a functionally equivalent part thereof, and (II) an amino acid sequence which is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the amino acid sequence or the part thereof under (I), preferably over the entire length of the amino acid sequence or the part thereof, and is functionally equivalent to the amino acid sequence or the part thereof under (I).

In a preferred embodiment, the recombinant protein of the present invention does not comprise a signal sequence at the amino-terminal end. For example, in a preferred embodiment, the recombinant protein of the present invention is derived from, preferably comprises, preferably essentially consists of, preferably consists of an amino acid sequence set forth in SEQ ID NO: 5 or 6 lacking the amino-terminal signal sequence, e.g., lacking the amino-terminal 23 amino acids, or a functionally equivalent part or variant thereof.

In a further aspect, the present invention provides a polynucleotide comprising a nucleic acid sequence encoding the recombinant protein of the present invention. The polynucleotide of the present invention may further comprise a nucleic acid sequence encoding a leader or signal sequence. Such sequence may, for example, mediate the transport of a protein into or through a membrane, for example, into or through the membrane of the endoplasmatic reticulum. Preferably, the polynucleotide is RNA, preferably in vitro transcribed RNA (IVT RNA).

In a preferred embodiment, the nucleic acid sequence encoding the recombinant protein of the present invention is derived from, preferably comprises, preferably essentially consists of, preferably consists of a nucleic acid sequence selected from the group consisting of:

(I) the nucleic acid sequences set forth in SEQ ID NOs: 10 and 11, or a part thereof which encodes a protein that is functionally equivalent to the protein encoded by the nucleic acid sequence set forth in SEQ ID NOs: 10 or 11, and (II) an nucleic acid sequence which is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the nucleic acid sequence or the part thereof under (I), preferably over the entire length of the nucleic acid sequence or the part thereof, and is functionally equivalent to the protein encoded by the nucleic acid sequence set forth in SEQ ID NOs: 10 or 11.

Preferably, the polynucleotide of the present invention comprises the nucleic acid sequence encoding the recombinant protein of the present invention as specified above and is RNA, preferably IVT RNA.

In a further aspect, the present invention provides a vector comprising the polynucleotide of the present invention. The vector may be any vector known in the art, for example, as described above. In a particular preferred embodiment, the vector is suitable as template for in vitro transcription, i.e., for the generation of IVT RNA, for example, using an RNA polymerase such as the T7, T3, or SP6 RNA polymerase.

In another aspect, the present invention provides a host cell comprising the polynucleotide or the vector of the present invention. In a preferred embodiment, the recombinant protein of the present invention encoded by the polynucleotide or the vector of the present invention is expressed in said host cell. In another embodiment, the recombinant protein of the present invention encoded by the polynucleotide or the vector of the present invention is not expressed in said host cell. In this case, the host cell, such as an E. coli cell, may, for example, be used for amplification of the vector or the polynucleotide of the present invention. Preferably, the recombinant protein of the present invention is located to the plasma membrane of the host cell. In the context of a host cell, the recombinant protein of the present invention preferably comprises an extracellular region, a transmembrane region, and an intracellular or cytoplasmic region. Preferably, the amino acid sequence of an intracellular segment of CD40 is located within the cytoplasmic region and the amino acid sequence mediating the association of the recombinant protein with the constant region of an immunoglobulin heavy chain is located within the extracellular region of the recombinant protein of the present invention.

In a preferred embodiment, the host cell expresses immunoglobulin chains, such as an immunoglobulin heavy chain and an immunoglobulin light chain. Thus, preferably the host cell is able of generating immunoglobulins, e.g., an antibody or a surface or membrane immunoglobulin, depending on whether the immunoglobulin heavy chain comprises a transmembrane domain. For example, the host cell may endogenously express immunoglobulin chains or the host cell may be transfected, preferably stably transfected, with a polynucleotide encoding immunoglobulin chains.

In a preferred embodiment, the host cell is a B cell, preferably a B cell carrying a BCR on its surface. Preferably, the host cell is a $CD19^+$ B cell, and preferably the host cell is human. Thus, in a preferred embodiment, the host cell is a human B cell.

In further aspects, the present invention provides methods using the recombinant protein, the polynucleotide, the vector, and/or the host cells of the present invention. The recombinant protein, the polynucleotide, the vector, and/or the host cells of the present invention allow for a completely new approach for activating B cells, i.e., for inducing proliferation, in particular clonal expansion, and differentiation of B cells into antibody secreting B cells. Without being bound by any theory, it is assumed that the recombinant protein of the present invention transforms the antigen-independent co-stimulatory CD40/CD40L signal which is needed for full B cell activation into an antigen-dependent signal. The recombinant protein of the present invention associates with immunoglobulin chains, in particular with one immunoglobulin heavy chain which is associated with an immunoglobulin light chain, at the plasma membrane of a host cell, preferably a B cell. This hetero-complex comprises an immunoglobulin variable region, in particular a hypervariable region, which is specific for a certain antigen, within the extracellular region of the hetero-complex, and a cytoplasmic region derived from the intracellular segment of CD40. Thus, binding of the respective antigen to the immunoglobulin variable region triggers the intracellular CD40 signaling cascade resulting in proliferation and differentiation of the B cell into an antibody secreting B cell.

Thus, the present invention allows for the specific activation of B cells having a predetermined antigen-specificity. In particular, the present invention provides tools for the selective expansion of a specific, preferably clonal, population of B cells and their differentiation into antibody secreting B cells. The selective expansion of specific B cells, i.e., the selective induction of proliferation of specific B cells, allows for the identification and isolation of B cells having a particular antigen-specificity from a mixture of B cells such as from the B cell repertoire of a subject. The identified and isolated B cells having a particular antigen-specificity may be further expanded, and antibodies, preferably secreted antibodies, may be obtained from said B cells and/or from the culture medium of said B cells. If the B cells are of human origin the antibodies generated by said B cells are fully human and are thus excellently suited for human immunotherapy. Thus, the recombinant protein, the polynucleotide, and/or the vector of the present invention may be used for the generation of fully human antibodies specific for a particular antigen, for example, specific for a tumor-associated antigen. It is particularly preferred that the antibodies are monoclonal, i.e., derived from a single B cell clone.

The present invention provides a completely new strategy for generating antibodies, preferably fully human monoclonal antibodies, which are useful for immunotherapy. This new strategy comprises the steps of expressing the recombinant protein of the present invention in B cells and contacting said B cells with an antigen of interest.

Thus, in one aspect, the present invention provides a method for inducing clonal expansion of a B cell specific for an antigen of interest, comprising the steps of:
(i) expressing in B cells the recombinant protein of the present invention, and
(ii) contacting the B cells of (i) with the antigen of interest.

In another aspect, the present invention provides a method for producing B cells secreting antibodies specific for an antigen of interest, comprising the steps of:
(i) expressing in B cells the recombinant protein of the present invention, and
(ii) contacting the B cells of (i) with the antigen of interest.

In this context, term "expressing in B cells the recombinant protein" preferably means that a polynucleotide encoding said protein, e.g., a polynucleotide or a vector of the present invention, is transcribed, in particular the nucleic acid sequence encoding the recombinant protein of the invention, and that the transcribed nucleic acid sequence is translated into the recombinant protein of the present invention. In case the polynucleotide encoding said protein is RNA, preferably IVT RNA, this term means that said RNA is translated into the recombinant protein of the present invention. Preferably, the recombinant protein of the present invention is expressed on the surface of the B cells, i.e., is localized to the plasma membrane of the B cells.

In preferred embodiments of the methods of the present invention, the B cells carry a BCR on their surface. Preferably, the B cells are CD19+ B cells, and preferably the B cells are human. Thus, in a preferred embodiment, the B cells are human CD19+ B cells which preferably carry a BCR on their surface. It is particularly preferred that the B cells in step (i) are a mixture of B cells comprising a multitude of antigen-specificities, preferably comprising the B cell repertoire of a subject or a portion thereof, preferably a substantial portion thereof.

In preferred embodiments, prior to step (i) the B cells are harvested from a subject, preferably a human subject. Preferably, the B cells are harvested from peripheral blood of the subject, preferably by density gradient centrifugation and magnetic cell sorting, preferably using antibodies specific for B cell surface protein such as antibodies directed to the BCR, CD19, CD20, or CD21. Such antibodies may be coupled to magnetic beads.

For example, peripheral blood mononuclear cells (PBMCs) may be isolated from buffy coats by density gradient centrifugation, e.g., using Ficoll Hypaque separation. B cells may then be purified by magnetic cell sorting using antibodies specific for B cell surface proteins such as anti-CD19-antibodies coupled to magnetic beads. Preferably, the isolated B cell population has a purity of at least 60%, at least 70%, at least 80%, at least 90%, at least 95%, or at least 98%. In this context, a purity of at least 60% means that at least 60% of the isolated cell population are B cells, preferably CD19+ B cells.

In preferred embodiments of the methods of the present invention, the B cells are transfected with a polynucleotide comprising a nucleic acid encoding the recombinant protein of the present invention to express said protein. For example, the transfection may be performed by a transfection method selected from the group consisting of electroporation, liposome-based transfection, calcium phosphate-based transfection, nucleofection, virus- or virus particle-based transfection, cationic polymer-based transfection (DEAE-dextran or polyethylenimine), protein-mediated transfection, magnet-assisted transfection, gene gun, and optical transfection. Preferably, the transfection method is electroporation. Preferably, the polynucleotide which is transfected is RNA, preferably in vitro transcribed RNA (IVT RNA). For example, electroporation may be performed using between 1 μg and 50 μg, preferably between 5 μg and 40 μg, more preferably between 10 μg and 30 μg, preferably about 20 μg IVT RNA per $1 \times 10^6$-$2 \times 10^7$ cells. Preferably, the electroporation parameters are 500 V and 100 μF.

Thus, in a preferred embodiment of the methods of the present invention, B cells, preferably human B cells, are transfected with RNA, preferably in vitro transcribed RNA, using electroporation. In a particularly preferred embodiment, B cells are harvested from a subject, preferably a human subject, preferably as described above, and said B cells are transfected with the polynucleotide or the vector of the present invention, preferably as described above.

The antigen in step (ii) of the methods of the present invention may be in solution or may be immobilized or may be both in solution and immobilized. For example, the antigen may be immobilized on a culture plate, such as a tissue culture plate. Preferably, the antigen is immobilized by antigen-specific antibodies which are immobilized on the culture plate. For example, for contacting the B cells with the antigen of interest in step (ii), the B cells may be cultured in a culture plate in which the antigen of interest has been immobilized. For example, the B cells may be cultured, preferably under conventional culture conditions, for a time period between 1 to 20 days, preferably between 2 to 15 days, more preferably between 3 to 10 days, such as for 3, 4, 5, 6, 7, 8, 9, or 10 days, preferably for 5 days.

In a preferred embodiment, the B cells are further contacted with cytokines in step (ii), preferably with cytokines promoting B cell activation, such as interleukin 4 (IL4) and/or interleukin 21 (IL21). Preferably, IL4 is added to the medium, preferably in an concentration ranging from 200 U/ml to 2000 U/ml, preferably 500 U/ml to 1500 U/ml, such as 500 U/ml, 600 U/ml, 700 U/ml, 800 U/ml, 900 U/ml, 1000 U/ml, 1100 U/ml, 1200 U/ml, 1300 U/ml, 1400 U/ml, or 1500 U/ml, preferably 1000 U/ml. Preferably, IL21 is added to the medium in an concentration ranging from 5 ng/ml to 500 ng/ml, from 10 to 200 ng/ml, from 20 to 100 ng/ml, such as 20 ng/ml, 30 ng/ml, 40 ng/ml, 50 ng/ml, 60 ng/ml, 70 ng/ml, 80 ng/ml, 90 ng/ml, or 100 ng/ml, preferably 50 ng/ml. Thus, in a preferred embodiment, the B cells are contacted with the antigen of interest and cytokines in step (ii), e.g., the B cells are cultured in presence of the antigen of interest and cytokines in step (ii).

In particularly preferred embodiments of the methods of the present invention, the B cells are not contacted with T cells or CD40 ligand (CD40L).

In preferred embodiments, the methods of the present invention further comprise the step of (iii) isolating proliferating B cells. The skilled person is well aware of how to identify proliferating cells such as proliferating B cells. For example, the B cells may be labeled with a fluorescent dye which changes its fluorescence intensity upon cell division, i.e., proliferation, such as with carboxyfluorescein succinimidyl ester (CFSE). CFSE can be used to monitor cell proliferation, in particular lymphocyte proliferation due to the progressive halving of CFSE fluorescence within daughter cells following each cell division. Approximately seven to eight cell divisions can be identified using CFSE before its fluorescence is too low. The fluorescence intensity of CFSE may be detected using flow cytometric analyses.

In particularly preferred embodiments, the methods of the present invention comprise the steps of harvesting B cells, preferably CD19+ B cells, from a subject, preferably a human subject, wherein preferably the B cells are a mixture of B cells comprising the entire B cell repertoire of said subject or a substantial portion thereof, transfecting said B cells with a polynucleotide comprising a nucleic acid encoding the recombinant protein of the present invention, wherein preferably the transfection is performed by electroporation, preferably using IVT RNA, expressing the recombinant protein of the present invention in the B cells, contacting the B cells with an antigen of interest, and preferably isolating proliferating B cells.

Preferably, the methods further comprise the step of cloning proliferating B cells, for example, by limiting dilution. The single proliferating B cell clones may then be further expanded and antibodies produced from said B cell clones may be obtained.

Thus, in a further aspect, the present invention provides a method for producing antibodies specific to an antigen of interest, said method comprising the steps of:

(i) inducing clonal expansion of B cells or producing B cells secreting antibodies according to the above methods of the present invention, and (ii) obtaining antibodies produced by the B cells.

In a preferred embodiment, the method for producing antibodies further comprises the steps of selecting proliferating B cells, preferably selecting a clone of the proliferating B cells, and culturing said selected proliferating B cells prior to step (ii). The step of selecting proliferating B cells may be performed as explained above for the step of isolating proliferating B cells, for example, using CFSE for identification of proliferating B cells.

The step of obtaining antibodies produced by the B cells may be performed by any art known technique for antibody isolation and/or purification. It is particularly preferred that the antibody produced by the B cells is secreted and is thus found in the culture medium of the B cells. Thus, in a preferred embodiment, the antibodies specific for an antigen of interest are isolated and/or purified from the culture medium of the B cells. For example, the culture medium may be applied to chromatography column comprising protein A or protein G coupled chromatography beads. According to a protocol for the purification of antibodies from serum or cell culture medium using the synthetic protein A absorbent MAbsorbent A2P (ProMetic BioSciences, Isle of Man), clarified serum or cell culture medium is loaded directly onto the affinity column without prior adjustment and albumin and unwanted debris are washed from the column with phosphate buffered saline (PBS), pH 7.5 before elution of bound antibodies with PBS at lowered pH or by using PEG. Other suitable protocols can be found in Antibodies: A Laboratory Manual, Eds. Edward Harlow and David Lane, Cold Spring Harbor Press (1988) which is incorporated herein by reference.

In a preferred embodiment, the B cells are of human origin and the B cells from which the antibodies are obtained are derived from a single B cell clone. Thus, in a preferred embodiment, the method of this aspect of the present invention is for producing human monoclonal antibodies specific for an antigen of interest, for example, for a tumor-associated antigen.

In one embodiment, the selected or isolated B cell clone, preferably secreting antibodies specific for an antigen of interest, may be fused, for example, with a myeloma cell for immortalization of the specific B cell clone. In this context, conventional hybridoma techniques known to somebody skilled in the art may be used.

The antibodies produced using the method of this aspect of the present invention may be used for immunotherapy, for example, for tumor immunotherapy, immunotherapy of infectious diseases such as for passive immunization, or for immunotherapy of immune disorders such as autoimmune diseases, e.g., rheumatoid arthritis. In one embodiment, the B cells are harvested from a patient and the antibodies produced using the method of the present invention are used for the immunotherapy of the patient the B cells were derived from.

Furthermore, the methods of the present invention may be used for further analysis, for example, for obtaining sequence data of the antigen-specific antibodies produced by the B cells. This information may be useful for the generation of recombinant antigen-producing cells.

Thus, the present invention provides the tools for a completely new approach for the generation of antigen-specific antibodies, preferably for the generation of human, preferably monoclonal antibodies.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Example 1

Recombinant Proteins of the Present Invention

To reproduce the CD40 signal we have generated novel fusion proteins, termed BZ1 (SEQ ID NOs: 5 and 10) and BZ2 (SEQ ID NOs: 6 and 11). These proteins have an extracellular fragment derived from the constant region of human IgG1 comprising the CH2 and CH3 domains (SEQ ID NO: 2 or 19) and an N-terminal marker domain composed of two c-myc epitope-tags (EQKLISEEDL; SEQ ID NO: 7) separated by a hemagglutinin (HA) sequence (YPYDVPDYA; SEQ ID NO: 8), as well as a transmembrane (TM) domain, which differs between the two constructs. While the BZ1 construct carries the TM domain of CD40 (SEQ ID NO: 4), the TM domain of the BZ2 construct is derived from a B cell receptor (BCR) (SEQ ID NO: 3). The C-terminus of the constructs comprises the cytoplasmic domain of human CD40 responsible for intracellular signal transduction (SEQ ID NO: 1) (FIG. 2).

Thus, the amino acid sequence set forth in SEQ ID NO: 5 comprises the following elements: aa 1-23=IL-2 secretion signal, aa 26-54=Myc-HA-Myc tag, aa 55-295=IgG1 CH2+CH3, aa 303-324=CD40 TM domain, aa 325-386=CD40 intracellular domain. The amino acid sequence set forth in SEQ ID NO: 6 comprises the following elements: aa 1-23=IL-2 secretion signal, aa 26-54=Myc-HA-Myc tag, aa 55-312=IgG1 CH2+CH3, aa 313-333=sequence comprising the IgG TM domain, and aa 334-395=CD40 intracellular domain.

The BZ constructs work as capture proteins. In the endoplasmic reticulum, the BZ proteins associate with immunoglobulin chains and the protein complexes are transported to the cell surface. This complex is able to bind a specific antigen via the variable region of the immunoglobulin chains and mimics a CD40 induced signal via the recombinant proteins of the invention. Therefore, after transfection of B cells with a polynucleotide comprising an amino acid sequence encoding the recombinant proteins of the present invention, e.g., the BZ1 or BZ2 construct, the CD40 signal is transformed from a natural antigen-independent to an artificial antigen-dependent signal (FIG. 3).

Example 2

In Vitro System for B Cell Activation

To reproduce the two step model of full B cell activation a novel in vitro system has been generated (FIG. 4). While the CD40 mediated signal is provided by the BZ constructs described above, the BCR mediated signal is based on the recognition of antigen which is preferably immobilized. The antigen is bound by a capture antibody that adheres to the culture dish. To further increase the similarities of the in vitro system with the in vivo B cell activation by T helper cells we also add the cytokines IL4 and IL21 to the medium.

$CD19^+$ B cells are isolated from peripheral blood of healthy donors or patients by Ficoll density gradient centrifugation and followed by magnetic cell sorting (MACS, Miltenyi, Bergisch Gladbach, Germany). A purity of more than 98% may be achieved by said procedure. The isolated B cells are transfected preferably by electroporation with in vitro transcribed RNA (IVT-RNA). The CD19+ B cells are labeled with CFSE (carboxyfluorescein succinimidyl ester; Invitrogen, Karlsruhe, Germany) and added to cell culture dishes in which specific antibodies for CD40, cmyc, irrelevant targets (control), or specific antigens are coated. The CFSE irreversibly binds to the cellular proteins and will distribute equally when the cells divide. The B cell proliferation is analyzed on day 5 by flow cytometry (FIG. 5).

This procedure represents a completely new strategy to expand antigen-specific B cells. By transfection of a large number of B cells the B cell repertoire e.g. of a patient or a pooled B cell fraction can be screened for B cells of defined reactivity. Through association of immunoglobulin chains with BZ protein the antigen-independent CD40 signal is transformed into an antigen-dependent signal. Thus, it is possible to screen a polyclonal B cell population and activate monoclonal B cells. Antigen-specific B cells, their B cell receptors and the antibodies produced by such B cells can be isolated. Such antibodies are highly useful for immunotherapy applications, e.g., for tumor immunotherapy.

Example 3

Expression of Recombinant Proteins of the Present Invention in Primary B Cells

B cells have been isolated from healthy donors. PBMC were isolated from buffy coats by Ficoll Hypaque (GE Healthcare, München, Germany) separation (780×g, 25 min, room temperature). B cells were purified by magnetic cell sorting (Miltenyi Biotec, Bergisch Gladbach, Germany) using anti-CD19-coupled magnetic beads (Miltenyi Biotec, Bergisch-Gladbach, Germany). Briefly, $5 \times 10^8$ PBMC in 4 mL PBS, 5 mM EDTA and 5% v/v human albumin (MACS buffer) were incubated for 10 min on ice with 600 µL anti-CD19-beads. After incubation, the cells were washed twice with MACS buffer and resuspended in 3 mL MACS buffer. CD19$^+$ B cells were separated by magnetic positive selection with LS+ columns (Miltenyi Biotec Bergisch-Gladbach, Germany). The isolated B cell population had a purity of more than 98% (Internal experimental quality control).

Purified B cells were washed and diluted in X-Vivo 15 (BioWhittaker/Cambrex, East Rutherford, USA). The electroporation was performed with 20 µg in-vitro transcribed RNA (IVT RNA) per $1 \times 10^6$-$2 \times 10^7$ cells. The electroporation parameters were optimized in a previous experiment (optimization data not shown). All B cells were electroporated with 500 V and 100 µF. The cells were resuspended in complete medium and rested for 1 h at 37° C. in medium.

The expression of the recombinant proteins in primary B cells was verified by Western blot analysis of the cell extract of transfected B cells (FIG. 6).

Example 4

Induction of Proliferation of Primary B Cells Expressing Recombinant Proteins of the Present Invention Purified and transfected CD19$^+$ B cells as described above were washed in RPMI medium and centrifuged (10 min; 450×g, RT). The pellet was resuspended in 0.1% BSA/PBS at room temperature and the cell number was adjusted to $5 \times 10^7$ cells/ml. The cell suspension was transferred to 50 ml reaction tubes and CFSE solution (Invitrogen, Karlsruhe, Germany) was added to a final concentration of 10 µM. The cell suspension was incubated for 10 min at 37° C. with gentle agitation and the reaction was stopped by adding ice cold RPMI medium. The cells were washed twice with pure FCS and twice with RPMI medium.

The succinimidyl ester of carboxyfluorescein diacetate (CFSE) irreversibly binds to both, intracellular and cell surface proteins by reacting with lysine side chains and other amine groups. When the cells divide, CFSE labeling is distributed equally between the daughter cells, thus the fluorescence intensity of the daughter cells is reduced by 50% compared to the parent generation. As a result, the cellular fluorescence intensity is indicative for number of cell divisions such that each successive generation in a population of proliferating cells is easily followed by flow cytometry.

The B cells were stimulated and expanded by cultivation with plate-bound antibodies and by the addition of the cytokines IL4 (1000 U/ml) (Miltenyi, Bergisch Gladbach, Germany) and IL21 (50 ng/ml) (Promokine, Heidelberg, Germany). The plates were coated with anti-CD40 (MAB89), anti-c-myc (9E10), irrelevant antibody (anti-CD3), or pure medium. Unbound antibodies were removed by washing. The BZ-transfected CFSE-labeled B cells were added to the antibody coated culture dishes and incubated for 5 days. The read out was performed by flow cytometric analyses (FIG. 7).

Example 5

Association of Recombinant Proteins of the Present Invention with Endogenous Immunoglobulin Chains in CHO-pC15 Cells Analyzed by Western Blot Analysis To analyze the ability of the recombinant proteins of the present invention to heterodimerize with immunoglobulin chains we used the CHO-pC15 cell line. This cell line is derived from the CHO-K1 WT cell line (ATCC No. CCL-61) and is stably transfected with the light and heavy chains of a human monoclonal antibody. This antibody is continuously produced and secreted.

CHO-K1 WT and CHO-pC15 cells were transfected with IVT RNAs encoding the BZ1 and the BZ2 proteins, respectively, using electroporation. Cells were harvested 24 h post transfection with 2 mM EDTA/PBS, washed with PBS, and stored as pellets at −80° C. The pellets were resuspended in Roti-reducing buffer or Roti-non-reducing buffer (both Carl Roth GmbH, Karlsruhe, Germany). The cell lysates were incubated for 15 min at 95° C. for reducing or at 65° C. for non-reducing conditions. For DNA digestion, 2% to 5% (v/v) Benzonase (Novagen (Merck), Darmstadt, Germany) were added and incubated for 15 min at room temperature.

Samples were separated on a polyacrylamide gel (4-12% gradient gel, Invitrogen). Samples were separated by electrophoresis (130 V, 100 mA, ca. 1.5-2.5 h) and subsequently blotted under semi-dry conditions (23 V, 300 mA, 45 min) onto a PVDF membrane (PALL, Port Washington, USA). The membranes were blocked with 10% nonfat dry milk in PBS including 0.1% Tween at 4° C. overnight. The membranes were incubated with the indicated primary antibodies (concentration according to manufacturer's instructions) followed by horseradish peroxidase-conjugated goat-anti-mouse IgG Fc specific secondary antibody (Sigma, concentration according to manufacturer's instructions). Both antibody incubation steps were carried out at room temperature for 1 h. The membranes were washed between both antibody incubation steps and after the secondary antibody incubation. The blots were developed using ECL-reagent (Amersham Biotech, Cardiff, UK) (FIG. 9).

The Western blot experiments under non reducing conditions resulted in a distinct protein band of 119 kDa which was detectable both using the anti-kappa (endogenous immunoglobulin chain) as well as the anti-c-myc (recombinant protein of the present invention) antibodies, but which was not detectable in untransfected CHO cells. This result indicates that the recombinant protein of the present invention indeed associates with endogenous immunoglobulin chains in cells.

To demonstrate that this distinct protein band of 119 kDa indeed represents the heterodimer of BZ protein and endogenous immunoglobulin chain, recovery experiments have been performed. To this end, a gel was loaded under non-reducing conditions with transfected and untransfected CHO-pC15 cell lysates and the separated proteins were blotted on a membrane. The 119 kDa band was excised and the proteins were eluted from the membrane. For the elution of the proteins, the dissected PVDF membrane parts were treated with 0.2-0.5 mL of elution buffer/cm$^2$ of PVDF strip. The elution buffer consisted of 2% SDS/1% Triton-X100 in 50 mM Tris-HCl, pH 9.5. The soaked membrane was mixed vigorously by vortexing for 10 min and centrifuged (5 min, 16000×g). The supernatant was mixed with Roti-reducing buffer, boiled (15 min, 95° C.), and directly used for SDS-PAGE under reducing conditions. The gel was blotted and subjected to Western blot analysis. The 119 kDa protein band obtained under non reducing conditions resulted in distinct protein bands that were detectable with anti-CD40, anti-c-myc (both part of BZ) and anti-kappa (endogenous immunoglobulin chain) antibodies under reducing conditions (FIG. 9C). This result shows that BZ constructs are indeed able to heterodimerize with endogenous immunoglobulin chains.

Example 6

Association of Recombinant Proteins of the Present Invention with Endogenous Immunoglobulin Chains in CHO-pC15 Cells Analyzed by Flow Cytometric Analysis For determining whether the complexes comprising a recombinant protein of the present invention in association with an immunoglobulin chain are located to the surface of cells, flow cytometric analyses on BZ1- or BZ2-transfected CHO-pC15 cells stably expressing immunoglobulin heavy and light chains were performed.

As a negative control, wild type CHO cells which do not express immunoglobulin chains have been transfected with BZ1- or BZ2-encoding polynucleotides. Strong expression of BZ1 and BZ2, respectively, was observed for the transfected wild type CHO cells analyzed by anti-c-myc staining, and no immunoglobulin light chain staining was detected on the surface said cells. By contrast, immunoglobulin chain (IgG) producing CHO-pC15 cells transfected with BZ1- or BZ2-encoding polynucleotides show a high percentage of cells with double positive staining for the BZ protein (anti-c-myc antibody) and the immunoglobulin chain (anti-kappa antibody), whereas immunoglobulin chain staining is not detectable for untransfected CHO-pC15 cells (FIG. 8B). This experiment shows that the BZ proteins are indeed capable of associating with immunoglobulin chains on the surface of cells.

Example 7

NF-κB Signaling in Cells Expressing a Recombinant Protein of the Present Invention A hallmark of CD40 induced signal transduction is the activation of the transcription factor NF-κB. This activation requires the clustering of the internal CD40 domain. To prove the functionality of the CD40 domain and thus, the signal transduction capability of the recombinant BZ proteins, the induction of BZ signaling in response to BZ clustering was monitored. To this end, the HEK293 cell line stably transfected with the lucNifty vector and miRNA81 was used. The lucNifty vector is a reporter plasmid including the luciferase gene under the control of an NF-κB-inducible ELAM1 composite promoter. The firefly luciferase from *Photinus pyralis* is a 61 kDa monomer which is functional after translation and catalyzes the oxidative enzymatic reaction from luciferin to oxyluciferin. This reaction requires ATP and $O_2$ as a substrate and produces light and AMP as a by-product. The produced light (550-570 nm) can be measured with a luminometer and corresponds to the activation level of NF-κB.

To perform the NFκB luciferase assays, HEK 293 reporter cells were transiently transfected with BZ constructs (20 µg/1×10$^6$ cells) and incubated in anti-cMyc or control antibody (anti-CD3) coated 96-well plates in 100 µl over night. 6 hours before analysis, PMA and Ionomycin were added as positive control. A mixture of D-luciferin (1 µg/µl) and 5 mM ATP-10 mM Tris base solution were added to each well and bioluminescence flux was measured using a microplate luminescence reader with 1 sec integration time/well.

Non-transfected HEK293 reporter cells show no bioluminescence. BZ1- and BZ2-transfected HEK293 reporter cells display a background signal (anti-CD3 and medium, both are negative controls) presumably resulting from homodimerized BZ constructs. The cross-linked BZ constructs induce a significant signal (FIG. 10).

These experiments demonstrate the functionality of the intracellular CD40 domain and the ability of the recombinant proteins of the present invention to recruit signaling factors.

Example 8

Induction of Proliferation of Peripheral CD19$^+$ B Cells Expressing a Recombinant Protein of the Present Invention For the activation and expansion of peripheral B cells transfected with BZ constructs, a monoclonal antibody against cMyc was coated on a plate or supplemented to the medium. Furthermore, the CD32 (Fc-gamma receptor) expressing cell line CHO-K1-CD32 and the cell line CHO-K1 WT, respectively, following treatment with Mitomycin C to inhibit proliferation were exposed to the antibody.

The B cells were transfected with RNA encoding either BZ1 (I) or BZ2 (II) (20 µg) or mock-transfected (III). 10 µg antibody in 100 µL PBS per well were incubated in a 96-well format for 2 hours at 37° C. After coating each well was washed with 200 µL medium to remove unbound antibodies. B cells labeled with CFSE to detect proliferation were added in a cell concentration of 2×10$^6$ cells/well and incubated for 5 days in complete culture medium supplemented with 5% human AB serum, IL4, and IL21. Subsequently the cells were harvested and analyzed by flow cytometry.

No proliferation was detected in the non-transfected B cells or BZ-transfected B cells cultivated with CHO-K1 cells (neg. contr.). The highest rate of proliferation was detected in anti-cMyc stimulations applied by antibody presented on CHO-K1-CD32 cells or coated to the dish (FIG. 11).

Example 9

Crosslinking of Recombinant Proteins of the Present Invention on the Surface of CD19$^+$ B Cells Induces Proliferation of Class Switched Memory B Cells CD19$^+$ B cells show the complete spectrum of B cell subpopulations. The main subpopulation consists of naïve B cells which are IgD$^+$IgM$^+$CD27$^-$IgG$^-$. Most of the antigen experienced B cells are memory B cells, which are mainly IgD$^-$IgM$^-$CD27$^+$IgG$^+$. Most of the peripheral plasma cells secrete IgG antibodies and have a IgD$^-$IgM$^-$CD27$^{++}$ phenotype.

For the activation and expansion of peripheral B cells transfected with BZ constructs an anti-cMyc antibody was used.

Non-transfected B cells were stimulated using an anti-CD40 MAB89 antibody. Both antibodies were coated on plates. 10 μg antibody in 100 μL PBS per well were incubated in a 96-well format for 2 hours at 37° C. After coating each well was washed with 200 μL medium to remove unbound antibodies. B cells were added in a cell concentration of $2 \times 10^6$ cells/well and incubated for 5 days in complete culture medium supplemented with 5% human AB serum, IL4, and IL21.

The stimulation with anti-CD40 antibody results in an activation of all subpopulations. IgM$^+$ and IgG$^+$ B cells proliferate to a similar extent. In contrast, BZ stimulation results in proliferation of IgD$^-$/IgM$^-$ cells and only few naïve IgM$^+$ B cells proliferate. The main population of memory B cells which proliferate are IgD$^-$. This data demonstrates that BZ constructs predominantly activate IgG$^+$ B cells (FIG. 12). Accordingly, one preferred B cell subpopulation according to the invention is IgG$^+$ B cells.

Example 10

Transient Activation of B Cells Expressing a Recombinant Protein of the Present Invention Peripheral B cells transfected with BZ constructs and non-transfected B cells were stimulated as described in Example 9. To analyze the activation pattern over the time and/or with increasing proliferation activated B cells were stained with an anti-CD25 antibody (activation marker).

The stimulation with anti-CD40 antibody results in a stable activation (constant CD25 expression over time). In contrast, BZ stimulation results in a transient activation. CD25 expression decreased with increasing proliferation (FIG. 13). This demonstrates that in the case of B cells isolated according to the present invention, activation is reversible and cells, e.g. following isolation, can regain their normal or inactive characteristics. This property of cells expressing a recombinant protein of the present invention is in particular beneficial for therapeutic strategies.

Example 11

Tetanus Specific Activation of IgG Memory B Cells Expressing a Recombinant Protein of the Present Invention Tetanus specific IgG$^+$ memory B cells transfected with BZ1 construct were stimulated with plate-coated tetanus toxoid (Calbiochem) or mock-stimulated. To this end, 10 μg tetanus toxoid in 100 μL PBS per well were incubated in a 96-well format for 2 hours at 37° C. After coating, each well was washed with 200 μL medium to remove unbound protein. CFSE labeled B cells were added in a cell concentration of $2 \times 10^6$ cells/well, incubated for 5 days in complete culture medium supplemented with 5% human AB serum, IL4, and IL21 and analyzed by flow cytometry.

BZ-transfected tetanus stimulated B cells show a higher proliferation rate compared to non-stimulated cells (FIG. 14).

Example 12

CMV Specific Activation of IgG$^+$ Memory B Cells Expressing a Recombinant Protein of the Present Invention CMV specific IgG$^+$ memory B cells from CMV infected patients transfected with BZ1 construct were stimulated with plate-coated CMV protein pp150 or glycoprotein B (gB) (Abcam) or mock-stimulated. CMV proteins were coated on the plates as described in Example 11. CFSE labeled B cells were added in a cell concentration of $2 \times 10^6$ cells/well, incubated for 5 days in complete culture medium supplemented with 5% human AB serum, IL4, and IL21 and analyzed by flow cytometry.

BZ-transfected CMV stimulated B cells show a higher proliferation rate compared to non-stimulated cells (FIG. 15).

The invention claimed is:

1. A method for inducing clonal expansion of a B cell specific for an antigen of interest, comprising the steps of:
   (i) expressing in a population of B cells comprising a multitude of antigen-specificities the recombinant protein comprising:
   (a) an amino acid sequence of an intracellular segment of CD40 comprising the amino acid sequence set forth in SEQ ID NO: 1, and
   (b) an amino acid sequence mediating the association of the recombinant protein with the constant region of an immunoglobulin heavy chain comprising the amino acid sequence set forth in SEQ ID NO: 2,
   wherein the amino acid sequences under (a) and (b) are linked via
   (c) an amino acid sequence comprising the amino acid sequence of a transmembrane domain, comprising the amino acid sequence set forth in SEQ ID NO: 3 or 4, and
   (ii) selectively activating B cells with specificity for an antigen of interest by contacting the population of B cells of (i) with said antigen of interest under conditions allowing binding of said antigen of interest to a heterocomplex comprising said recombinant protein and an immunoglobulin variable region which is specific for the antigen of interest, thereby triggering the intracellular CD40 signaling cascade resulting in proliferation and differentiation of the B cell into an antibody secreting B cell, and
   (iii) cultivating the B cells of (ii), thereby clonally expanding said activated B cells with specificity for the antigen of interest.

2. A method for producing B cells secreting antibodies specific for an antigen of interest, comprising the steps of:
   (i) expressing in a population of B cells comprising a multitude of antigen-specificities the recombinant protein comprising:
   (a) an amino acid sequence of an intracellular segment of CD40 comprising the amino acid sequence set forth in SEQ ID NO: 1, and
   (b) an amino acid sequence mediating the association of the recombinant protein with the constant region of an immunoglobulin heavy chain comprising the amino acid sequence set forth in SEQ ID NO: 2,
   wherein the amino acid sequences under (a) and (b) are linked via
   (c) an amino acid sequence comprising the amino acid sequence of a transmembrane domain comprising the amino acid sequence set forth in SEQ ID NO: 3 or 4, and
   (ii) selectively activating B cells with specificity for an antigen of interest by contacting the population of B cells of (i) with said antigen of interest under conditions allowing binding of said antigen of interest to a heterocomplex comprising said recombinant protein and an immunoglobulin variable region which is specific for the antigen of interest, thereby triggering the intracellular CD40 signaling cascade resulting in proliferation and differentiation of the B cell into an antibody secreting B cell,
   (iii) cultivating B cells of (ii), thereby clonally expanding activated B cells with specificity for the antigen of interest, and
   (iv) selecting a proliferating B cell clone.

3. The method of claim 1 or 2, wherein the B cells carry a BCR on their surface.

4. The method of any one of claim 1 or 2, wherein prior to step (i) the B cells are harvested from a subject.

5. The method of any one of claim 1 or 2, wherein the B cells are transfected with a polynucleotide comprising a nucleic acid encoding the recombinant protein.

6. The method of any one of claim 1 or 2, wherein in step (ii) the antigen is in solution or is immobilized.

7. A method for producing antibodies specific to an antigen of interest, said method comprising the steps of:
   (i) inducing clonal expansion of B cells or producing B cells secreting antibodies according to the method of claim 1 or 2, and
   (ii) obtaining antibodies produced by the B cells.

8. The method of claim 1 or 2, wherein the recombinant protein comprises an amino acid sequence as set forth in SEQ ID NO: 5 or 6.

* * * * *

SEQUENCE LISTING

<160> NUMBER OF SEQ ID NOS: 19

<210> SEQ ID NO 1
<211> LENGTH: 62
<212> TYPE: PRT
<213> ORGANISM: Homo sapiens

<400> SEQUENCE: 1

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 2
<211> LENGTH: 241
<212> TYPE: PRT
<213> ORGANISM: Homo sapiens

<400> SEQUENCE: 2

-continued

```
Arg Ser Asp Lys Lys Val Glu Pro Lys Ser Asp Lys Thr His Thr
1               5                   10                  15

Cys Pro Pro Cys Pro Ala Pro Glu Leu Leu Gly Gly Pro Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
        50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Glu Leu Gln Leu
225                 230                 235                 240

Glu

<210> SEQ ID NO 3
<211> LENGTH: 21
<212> TYPE: PRT
<213> ORGANISM: Homo sapiens

<400> SEQUENCE: 3

Ile Thr Ile Phe Ile Thr Leu Phe Leu Leu Ser Val Cys Tyr Ser Ala
1               5                   10                  15

Thr Val Thr Phe Phe
            20

<210> SEQ ID NO 4
<211> LENGTH: 22
<212> TYPE: PRT
<213> ORGANISM: Homo sapiens

<400> SEQUENCE: 4

Ala Leu Val Val Ile Pro Ile Ile Phe Gly Ile Leu Phe Ala Ile Leu
1               5                   10                  15

Leu Val Leu Val Phe Ile
            20

<210> SEQ ID NO 5
<211> LENGTH: 386
```

```
<212> TYPE: PRT
<213> ORGANISM: Artificial
<220> FEATURE:
<223> OTHER INFORMATION: recombinant protein BZ1

<400> SEQUENCE: 5
```

| | | | | | | | | | | | | | | |
|---|---|---|---|---|---|---|---|---|---|---|---|---|---|---|
| Met | Tyr | Arg | Met | Gln | Leu | Leu | Ser | Cys | Ile | Ala | Leu | Ser | Leu | Ala | Leu |
| 1 | | | | 5 | | | | | 10 | | | | | 15 | |
| Val | Thr | Asn | Ser | Ala | Pro | Thr | Gly | Ser | Glu | Gln | Lys | Leu | Ile | Ser | Glu |
| | | | 20 | | | | | 25 | | | | | 30 | | |
| Glu | Asp | Leu | Tyr | Pro | Tyr | Asp | Val | Pro | Asp | Tyr | Ala | Glu | Gln | Lys | Leu |
| | | | 35 | | | | 40 | | | | | 45 | | | |
| Ile | Ser | Glu | Glu | Asp | Leu | Arg | Ser | Asp | Lys | Lys | Val | Glu | Pro | Lys | Ser |
| | 50 | | | | | 55 | | | | | 60 | | | | |
| Ser | Asp | Lys | Thr | His | Thr | Cys | Pro | Pro | Cys | Pro | Ala | Pro | Glu | Leu | Leu |
| 65 | | | | | 70 | | | | | 75 | | | | | 80 |
| Gly | Gly | Pro | Ser | Val | Phe | Leu | Phe | Pro | Pro | Lys | Pro | Lys | Asp | Thr | Leu |
| | | | | 85 | | | | | 90 | | | | | 95 | |
| Met | Ile | Ser | Arg | Thr | Pro | Glu | Val | Thr | Cys | Val | Val | Val | Asp | Val | Ser |
| | | | | 100 | | | | | 105 | | | | | 110 | |
| His | Glu | Asp | Pro | Glu | Val | Lys | Phe | Asn | Trp | Tyr | Val | Asp | Gly | Val | Glu |
| | | | | 115 | | | | | 120 | | | | | 125 | |
| Val | His | Asn | Ala | Lys | Thr | Lys | Pro | Arg | Glu | Glu | Gln | Tyr | Asn | Ser | Thr |
| | 130 | | | | | 135 | | | | | 140 | | | | |
| Tyr | Arg | Val | Val | Ser | Val | Leu | Thr | Val | Leu | His | Gln | Asp | Trp | Leu | Asn |
| 145 | | | | | 150 | | | | | 155 | | | | | 160 |
| Gly | Lys | Glu | Tyr | Lys | Cys | Lys | Val | Ser | Asn | Lys | Ala | Leu | Pro | Ala | Pro |
| | | | | 165 | | | | | 170 | | | | | 175 | |
| Ile | Glu | Lys | Thr | Ile | Ser | Lys | Ala | Lys | Gly | Gln | Pro | Arg | Glu | Pro | Gln |
| | | | | 180 | | | | | 185 | | | | | 190 | |
| Val | Tyr | Thr | Leu | Pro | Pro | Ser | Arg | Asp | Glu | Leu | Thr | Lys | Asn | Gln | Val |
| | | | | 195 | | | | | 200 | | | | | 205 | |
| Ser | Leu | Thr | Cys | Leu | Val | Lys | Gly | Phe | Tyr | Pro | Ser | Asp | Ile | Ala | Val |
| | 210 | | | | | 215 | | | | | 220 | | | | |
| Glu | Trp | Glu | Ser | Asn | Gly | Gln | Pro | Glu | Asn | Asn | Tyr | Lys | Thr | Thr | Pro |
| 225 | | | | | 230 | | | | | 235 | | | | | 240 |
| Pro | Val | Leu | Asp | Ser | Asp | Gly | Ser | Phe | Phe | Leu | Tyr | Ser | Lys | Leu | Thr |
| | | | | 245 | | | | | 250 | | | | | 255 | |
| Val | Asp | Lys | Ser | Arg | Trp | Gln | Gln | Gly | Asn | Val | Phe | Ser | Cys | Ser | Val |
| | | | | 260 | | | | | 265 | | | | | 270 | |
| Met | His | Glu | Ala | Leu | His | Asn | His | Tyr | Thr | Gln | Lys | Ser | Leu | Ser | Leu |
| | | | | 275 | | | | | 280 | | | | | 285 | |
| Ser | Pro | Glu | Leu | Gln | Leu | Glu | Gly | Pro | Gln | Asp | Arg | Leu | Arg | Ala | Leu |
| | 290 | | | | | 295 | | | | | 300 | | | | |
| Val | Val | Ile | Pro | Ile | Ile | Phe | Gly | Ile | Leu | Phe | Ala | Ile | Leu | Leu | Val |
| 305 | | | | | 310 | | | | | 315 | | | | | 320 |
| Leu | Val | Phe | Ile | Lys | Lys | Val | Ala | Lys | Lys | Pro | Thr | Asn | Lys | Ala | Pro |
| | | | | 325 | | | | | 330 | | | | | 335 | |
| His | Pro | Lys | Gln | Glu | Pro | Gln | Glu | Ile | Asn | Phe | Pro | Asp | Asp | Leu | Pro |
| | | | | 340 | | | | | 345 | | | | | 350 | |
| Gly | Ser | Asn | Thr | Ala | Ala | Pro | Val | Gln | Glu | Thr | Leu | His | Gly | Cys | Gln |
| | | | 355 | | | | | 360 | | | | | 365 | | |
| Pro | Val | Thr | Gln | Glu | Asp | Gly | Lys | Glu | Ser | Arg | Ile | Ser | Val | Gln | Glu |
| | | | 370 | | | | | 375 | | | | | 380 | | |

Arg Gln
385

<210> SEQ ID NO 6
<211> LENGTH: 395
<212> TYPE: PRT
<213> ORGANISM: Artificial
<220> FEATURE:
<223> OTHER INFORMATION: recombinant protein BZ2

<400> SEQUENCE: 6

```
Met Tyr Arg Met Gln Leu Leu Ser Cys Ile Ala Leu Ser Leu Ala Leu
1               5                   10                  15

Val Thr Asn Ser Ala Pro Thr Gly Ser Glu Gln Lys Leu Ile Ser Glu
            20                  25                  30

Glu Asp Leu Tyr Pro Tyr Asp Val Pro Asp Tyr Ala Glu Gln Lys Leu
        35                  40                  45

Ile Ser Glu Glu Asp Leu Arg Ser Asp Lys Lys Val Glu Pro Lys Ser
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Asp Glu Leu Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Glu Leu Gln Leu Glu Glu Ser Cys Ala Glu Ala Gln Asp Gly
    290                 295                 300

Glu Leu Asp Gly Leu Trp Thr Thr Ile Thr Ile Phe Ile Thr Leu Phe
305                 310                 315                 320

Leu Leu Ser Val Cys Tyr Ser Ala Thr Val Thr Phe Phe Lys Val
                325                 330                 335

Ala Lys Lys Pro Thr Asn Lys Ala Pro His Pro Lys Gln Glu Pro Gln
            340                 345                 350
```

```
Glu Ile Asn Phe Pro Asp Asp Leu Pro Gly Ser Asn Thr Ala Ala Pro
            355                 360                 365
Val Gln Glu Thr Leu His Gly Cys Gln Pro Val Thr Gln Glu Asp Gly
        370                 375                 380
Lys Glu Ser Arg Ile Ser Val Gln Glu Arg Gln
385                 390                 395

<210> SEQ ID NO 7
<211> LENGTH: 10
<212> TYPE: PRT
<213> ORGANISM: Artificial
<220> FEATURE:
<223> OTHER INFORMATION: myc-tag

<400> SEQUENCE: 7

Glu Gln Lys Leu Ile Ser Glu Glu Asp Leu
1               5                   10

<210> SEQ ID NO 8
<211> LENGTH: 9
<212> TYPE: PRT
<213> ORGANISM: Artificial
<220> FEATURE:
<223> OTHER INFORMATION: HA-tag

<400> SEQUENCE: 8

Tyr Pro Tyr Asp Val Pro Asp Tyr Ala
1               5

<210> SEQ ID NO 9
<211> LENGTH: 30
<212> TYPE: PRT
<213> ORGANISM: Homo sapiens

<400> SEQUENCE: 9

Gly Glu Leu Asp Gly Leu Trp Thr Thr Ile Thr Ile Phe Ile Thr Leu
1               5                   10                  15

Phe Leu Leu Ser Val Cys Tyr Ser Ala Thr Val Thr Phe Phe
            20                  25                  30

<210> SEQ ID NO 10
<211> LENGTH: 1159
<212> TYPE: DNA
<213> ORGANISM: Artificial
<220> FEATURE:
<223> OTHER INFORMATION: nucleic acid sequence encoding recombinant
      protein BZ1

<400> SEQUENCE: 10
atgtaccgga tgcagctcct gtcctgcatc gccctgagcc tggccctggt gaccaacagc       60
gcccccaccg gatccgagca gaagctgatc agcgaagagg acctgtaccc ctacgacgtg      120
cccgactacg ccgaacagaa actgatctct gaagaggatc tgagatctga caagaaggtg      180
gagcccaaga gcagcgacaa gacccacacc tgccccccct gccctgcccc tgagctcctg      240
gggggaccca gcgtgttcct gttccccccc aagcccaagg acaccctgat gatcagccgg      300
acccccgagg tgacctgcgt ggtggtggac gtgagccacg aggaccctga ggtgaagttc      360
aattggtacg tggacggcgt ggaggtgcac aacgccaaga ccaagcccag agaggaacag      420
tacaacagca cctaccgggt ggtgtccgtg ctgaccgtgc tgcaccagga ctggctgaac      480
ggcaaagaat acaagtgcaa ggtgtccaac aaggcccctg ctgcccccat cgagaaaacc      540
atcagcaagg ccaagggcca gcctcgggag ccccaggtgt acaccctgcc ccctcccgg      600
```

```
gatgagctga ccaagaacca ggtgtccctg acctgcctgg tgaagggctt ctaccccagc      660
gacatcgccg tggagtggga gagcaacggc cagcccgaga caactacaa gaccaccccc       720 cctgtgctgg acagcgacgg cagcttcttc ctgtacagca agctgaccgt ggacaagagc      780
cggtggcagc agggcaacgt gttctcctgc tccgtgatgc acgaggccct gcacaaccac      840
tacacccaga agtccctgtc cctgagcccc gaactccagc tcgagggacc acaggaccgg      900
ctgagggccc tggtggtgat ccccatcatc ttcggcatcc tgttcgccat cctgctggtg      960
ctggtgttca tcaagaaagt ggccaaaaaa cctacaaaca aagcccctca ccctaaacag     1020
gaacctcagg aaattaactt tccagacgat ctgcctggct ccaatacagc cgccccagtg     1080
caggaaacac tgcacggctg tcagcctgtg acacaggaag atgggaaaga agccggatc      1140 tctgtgcagg aacgccagt                                                  1159
```

<210> SEQ ID NO 11
<211> LENGTH: 1185
<212> TYPE: DNA
<213> ORGANISM: Artificial
<220> FEATURE:
<223> OTHER INFORMATION: nucleic acid sequence encoding recombinant protein BZ2

<400> SEQUENCE: 11

```
atgtaccgga tgcagctcct gtcctgcatc gccctgagcc tggccctggt gaccaacagc       60
gcccccaccg gatccgagca gaagctgatc agcgaagagg acctgtaccc ctacgacgtg      120
cccgactacg ccgaacagaa actgatctct gaagaggatc tgagatctga caagaaggtg      180
gagcccaaga gcagcgacaa gacccacacc tgcccccct gccctgcccc tgagctcctg       240
ggggacccca gcgtgttcct gttccccccc aagcccaagg acaccctgat gatcagccgg      300
acccccgagg tgacctgcgt ggtggtggac gtgagccacg aggaccctga ggtgaagttc      360
aattggtacg tggacggcgt ggaggtgcac aacgccaaga ccaagcccag agaggaacag      420
tacaacagca cctaccgggt ggtgtccgtg ctgaccgtgc tgcaccagga ctggctgaac      480
ggcaaagaat acaagtgcaa ggtgtccaac aaggccctgc ctgcccccat cgagaaaacc      540
atcagcaagg ccaagggcca gcctcgggag ccccaggtgt acaccctgcc ccctcccgg      600 gatgagctga ccaagaacca ggtgtccctg acctgcctgg tgaagggctt ctaccccagc      660
gacatcgccg tggagtggga gagcaacggc cagcccgaga caactacaa gaccaccccc       720 cctgtgctgg acagcgacgg cagcttcttc ctgtacagca agctgaccgt ggacaagagc      780
cggtggcagc agggcaacgt gttctcctgc tccgtgatgc acgaggccct gcacaaccac      840
tacacccaga agtccctgtc cctgagcccc gaactccagc tcgaggaaag ctgcgccgag      900
gcccaggacg gcgagctgga cggcctgtgg accaccatca ccatcttcat caccctgttt      960
ctgctgtccg tgtgctacag cgccaccgtg acctttttta agaaggtggc caagaagccc     1020
accaataagg cccccccacc caagcaggaa cccaggaaa tcaacttccc cgacgacctg      1080
cccggcagca cacagccgc ccctgtgcag gaaaccctgc acggctgcca gcccgtgacc      1140
caggaagatg gcaaagagtc ccggatcagc gtccaggaac ggcag                    1185
```

<210> SEQ ID NO 12
<211> LENGTH: 599
<212> TYPE: PRT
<213> ORGANISM: Homo sapiens

<400> SEQUENCE: 12

-continued

```
Met Ser Val Ser Phe Leu Ile Phe Leu Pro Val Gly Leu Pro Trp
1               5                   10                  15

Gly Val Leu Ser Gln Val Gln Leu Gln Gln Ser Gly Pro Gly Leu Val
            20                  25                  30

Lys Pro Ala Gln Thr Leu Ser Leu Thr Cys Ala Ile Ser Gly Asp Ser
            35                  40                  45

Val Ser Ser Asn Ser Ala Thr Trp Asn Trp Ile Arg Gln Ser Pro Leu
50                  55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg Glu Asn Tyr Tyr Gly Ser Gly
            115                 120                 125

Arg Tyr Asn Trp Phe Asp Pro Trp Gly Gln Gly Thr Leu Val Thr Val
130                 135                 140

Ser Ser Gly Ser Ala Ser Ala Pro Thr Leu Phe Pro Leu Val Ser Cys
145                 150                 155                 160

Glu Asn Ser Pro Ser Asp Thr Ser Ser Val Ala Val Gly Cys Leu Ala
                165                 170                 175

Gln Asp Phe Leu Pro Asp Ser Ile Thr Phe Ser Trp Lys Tyr Lys Asn
            180                 185                 190

Asn Ser Asp Ile Ser Ser Thr Arg Gly Phe Pro Ser Val Leu Arg Gly
            195                 200                 205

Gly Lys Tyr Ala Ala Thr Ser Gln Val Leu Leu Pro Ser Lys Asp Val
210                 215                 220

Met Gln Gly Thr Asp Glu His Val Val Cys Lys Val Gln His Pro Asn
225                 230                 235                 240

Gly Asn Lys Glu Lys Asn Val Pro Leu Pro Val Ile Ala Glu Leu Pro
                245                 250                 255

Pro Lys Val Ser Val Phe Val Pro Pro Arg Asp Gly Phe Phe Gly Asn
            260                 265                 270

Pro Arg Lys Ser Lys Leu Ile Cys Gln Ala Thr Gly Phe Ser Pro Arg
            275                 280                 285

Gln Ile Gln Val Ser Trp Leu Arg Glu Gly Lys Gln Val Gly Ser Gly
290                 295                 300

Val Thr Thr Asp Gln Val Gln Ala Glu Ala Lys Glu Ser Gly Pro Thr
305                 310                 315                 320

Thr Tyr Lys Val Thr Ser Thr Leu Thr Ile Lys Glu Ser Asp Trp Leu
                325                 330                 335

Ser Gln Ser Met Phe Thr Cys Arg Val Asp His Arg Gly Leu Thr Phe
            340                 345                 350

Gln Gln Asn Ala Ser Ser Met Cys Val Pro Asp Gln Asp Thr Ala Ile
            355                 360                 365

Arg Val Phe Ala Ile Pro Pro Ser Phe Ala Ser Ile Phe Leu Thr Lys
370                 375                 380

Ser Thr Lys Leu Thr Cys Leu Val Thr Asp Leu Thr Thr Tyr Asp Ser
385                 390                 395                 400

Val Thr Ile Ser Trp Thr Arg Gln Asn Gly Glu Ala Val Lys Thr His
                405                 410                 415
```

```
Thr Asn Ile Ser Glu Ser His Pro Asn Ala Thr Phe Ser Ala Val Gly
            420                 425                 430

Glu Ala Ser Ile Cys Glu Asp Asp Trp Asn Ser Gly Glu Arg Phe Thr
        435                 440                 445

Cys Thr Val Thr His Thr Asp Leu Pro Ser Pro Leu Lys Gln Thr Ile
    450                 455                 460

Ser Arg Pro Lys Gly Val Ala Leu His Arg Pro Asp Val Tyr Leu Leu
465                 470                 475                 480

Pro Pro Ala Arg Glu Gln Leu Asn Leu Arg Glu Ser Ala Thr Ile Thr
                485                 490                 495

Cys Leu Val Thr Gly Phe Ser Pro Ala Asp Val Phe Val Gln Trp Met
        500                 505                 510

Gln Arg Gly Gln Pro Leu Ser Pro Glu Lys Tyr Val Thr Ser Ala Pro
    515                 520                 525

Met Pro Glu Pro Gln Ala Pro Gly Arg Tyr Phe Ala His Ser Ile Leu
530                 535                 540

Thr Val Ser Glu Glu Trp Asn Thr Gly Glu Thr Tyr Thr Cys Val
545                 550                 555                 560

Val Ala His Glu Ala Leu Pro Asn Arg Val Thr Glu Arg Thr Val Asp
                565                 570                 575

Lys Ser Thr Gly Lys Pro Thr Leu Tyr Asn Val Ser Leu Val Met Ser
        580                 585                 590

Asp Thr Ala Gly Thr Cys Tyr
        595

<210> SEQ ID NO 13
<211> LENGTH: 509
<212> TYPE: PRT
<213> ORGANISM: Homo sapiens

<400> SEQUENCE: 13

Glu Glu Gln Leu Glu Glu Ser Gly Gly Gly Val Val Gln Pro Gly Arg
1               5                   10                  15

Ser Leu Arg Leu Ser Cys Glu Ala Ser Gly Leu Arg Phe Ser Ile Tyr
            20                  25                  30

Gly Met Phe Trp Val Arg Gln Ala Pro Gly Lys Gly Leu Glu Trp Leu
        35                  40                  45

Ala Leu Ile Trp Asn Asp Gly Ser Arg Lys His Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Asp Thr Ala Val Tyr Phe Cys
                85                  90                  95

Gly Ser Gly Thr Thr Ala Phe Ser Gly Ala Ala Pro Asp Asn Tyr His
            100                 105                 110

Ile His Val Trp Gly Lys Gly Thr Thr Val Thr Val Ser Ser Ala Pro
        115                 120                 125

Thr Lys Ala Pro Asp Val Phe Pro Ile Ile Ser Gly Cys Arg His Pro
    130                 135                 140

Lys Asp Asn Ser Pro Val Val Leu Ala Cys Leu Ile Thr Gly Tyr His
145                 150                 155                 160

Pro Thr Ser Val Thr Val Thr Trp Tyr Met Gly Thr Gln Ser Gln Pro
                165                 170                 175

Gln Arg Thr Phe Pro Glu Ile Gln Arg Arg Asp Ser Tyr Tyr Met Thr
            180                 185                 190
```

-continued

```
Ser Ser Gln Leu Ser Thr Pro Leu Gln Gln Trp Arg Gln Gly Glu Tyr
        195                 200                 205

Lys Cys Val Val Gln His Thr Ala Ser Lys Ser Lys Lys Glu Ile Phe
210                 215                 220

Arg Trp Pro Glu Ser Pro Lys Ala Gln Ala Ser Ser Val Pro Thr Ala
225                 230                 235                 240

Gln Pro Gln Ala Glu Gly Ser Leu Ala Lys Ala Thr Thr Ala Pro Ala
                245                 250                 255

Thr Thr His Asn Thr Gly Arg Gly Gly Glu Glu Lys Lys Lys Glu Lys
                260                 265                 270

Glu Lys Glu Glu Gln Glu Glu Arg Glu Thr Lys Thr Pro Glu Cys Pro
                275                 280                 285

Ser His Thr Gln Pro Leu Gly Val Tyr Leu Leu Thr Pro Ala Val Gln
                290                 295                 300

Asp Leu Trp Leu Arg Asp Lys Ala Thr Phe Thr Cys Phe Val Val Gly
305                 310                 315                 320

Ser Asp Leu Lys Asp Ala His Leu Thr Trp Glu Val Ala Gly Lys Val
                325                 330                 335

Pro Thr Gly Gly Val Glu Glu Gly Leu Leu Glu Arg His Ser Asn Gly
                340                 345                 350

Ser Gln Ser Gln His Ser Arg Leu Thr Leu Pro Arg Ser Leu Trp Asn
                355                 360                 365

Ala Gly Thr Ser Val Thr Cys Thr Leu Asn His Pro Ser Leu Pro Pro
                370                 375                 380

Gln Arg Leu Met Ala Leu Arg Glu Pro Ala Ala Gln Ala Pro Val Lys
385                 390                 395                 400

Leu Ser Leu Asn Leu Leu Ala Ser Ser Asp Pro Pro Glu Ala Ala Ser
                405                 410                 415

Trp Leu Leu Cys Glu Val Ser Gly Phe Ser Pro Pro Asn Ile Leu Leu
                420                 425                 430

Met Trp Leu Glu Asp Gln Arg Glu Val Asn Thr Ser Gly Phe Ala Pro
                435                 440                 445

Ala Arg Pro Pro Pro Gln Pro Gly Ser Thr Thr Phe Trp Ala Trp Ser
                450                 455                 460

Val Leu Arg Val Pro Ala Pro Pro Ser Pro Gln Pro Ala Thr Tyr Thr
465                 470                 475                 480

Cys Val Val Ser His Glu Asp Ser Arg Thr Leu Leu Asn Ala Ser Arg
                485                 490                 495

Ser Leu Glu Val Ser Tyr Val Thr Asp His Gly Pro Met
                500                 505

<210> SEQ ID NO 14
<211> LENGTH: 325
<212> TYPE: PRT
<213> ORGANISM: Homo sapiens

<400> SEQUENCE: 14

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
                35                  40                  45

Val His Thr Phe Pro Ala Val Leu Gln Ser Ser Gly Leu Tyr Ser Leu
```

```
Ser Ser Val Val Thr Val Pro Ser Ser Asn Phe Gly Thr Gln Thr Tyr
 65                  70                  75                  80

Thr Cys Asn Val Asp His Lys Pro Ser Asn Thr Lys Val Asp Lys Thr
                 85                  90                  95

Val Glu Arg Lys Cys Cys Val Glu Cys Pro Pro Cys Pro Ala Pro Pro
            100                 105                 110

Val Ala Gly Pro Ser Val Phe Leu Phe Pro Pro Lys Pro Lys Asp Thr
            115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
            195                 200                 205

Pro Ile Glu Lys Thr Ile Ser Lys Thr Lys Gly Gln Pro Arg Glu Pro
210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
            275                 280                 285

Thr Val Asp Lys Ser Arg Trp Gln Gln Gly Asn Val Phe Ser Cys Ser
290                 295                 300

Val Met His Glu Ala Leu His Asn His Tyr Thr Gln Lys Ser Leu Ser
305                 310                 315                 320

Leu Ser Pro Gly Lys
            325

<210> SEQ ID NO 15
<211> LENGTH: 346
<212> TYPE: PRT
<213> ORGANISM: Homo sapiens

<400> SEQUENCE: 15

Phe Thr Lys Gly Pro Ser Val Phe Pro Leu Ala Pro Cys Ser Arg Ser
 1               5                  10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
 50                  55                  60

Ser Ser Val Val Thr Val Pro Ser Ser Leu Gly Thr Gln Thr Tyr
 65                  70                  75                  80

Thr Cys Asn Val Asn His Lys Pro Ser Asn Thr Lys Val Asp Lys Arg
                 85                  90                  95
```

```
Val Glu Leu Lys Thr Pro Leu Gly Asp Thr Pro Pro Cys Pro Arg
            100                 105                 110

Cys Pro Glu Pro Lys Ser Cys Asp Thr Pro Pro Cys Pro Arg Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Gln Phe Lys Trp
                165                 170                 175

Tyr Val Asp Gly Val Glu Val His Asn Ala Lys Thr Lys Leu Arg Glu
            180                 185                 190

Glu Gln Tyr Asn Ser Thr Phe Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Asn Thr Thr Pro Pro Met Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Ile Phe Ser Cys Ser Val Met His Glu Ala Leu His Asn Arg Tyr Thr
                325                 330                 335

Gln Lys Ser Leu Ser Leu Ser Pro Gly Lys
            340                 345

<210> SEQ ID NO 16
<211> LENGTH: 389
<212> TYPE: PRT
<213> ORGANISM: Homo sapiens
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (280)..(280)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid

<400> SEQUENCE: 16
```

```
Tyr Thr Gln Arg Phe Lys Asp Lys Ala Lys Leu Thr Ala Val Thr Ser
1               5                   10                  15

Ala Asn Thr Ala Tyr Met Glu Leu Ser Ser Leu Thr Asn Glu Asp Ser
            20                  25                  30

Ala Val Tyr Tyr Cys Ser Ile Ile Tyr Phe Asp Tyr Ala Asp Phe Ile
        35                  40                  45

Met Asp Tyr Trp Gly Gln Gly Thr Thr Val Thr Val Ser Thr Ala Ser
    50                  55                  60

Thr Lys Gly Pro Ser Val Phe Pro Leu Ala Pro Cys Ser Arg Ser Thr
65                  70                  75                  80

Ser Glu Ser Thr Ala Ala Leu Gly Cys Leu Val Lys Asp Tyr Phe Pro
                85                  90                  95

Glu Pro Val Thr Val Ser Trp Asn Ser Gly Ala Leu Thr Ser Gly Val
                100                 105                 110

His Thr Phe Pro Ala Val Leu Gln Xaa Ser Gly Leu Tyr Ser Leu Ser
            115                 120                 125

Ser Val Val Thr Val Pro Ser Ser Leu Gly Thr Lys Thr Tyr Thr
        130                 135                 140

Cys Asn Val Asp His Lys Pro Ser Asn Thr Lys Val Asp Lys Arg Val
145                 150                 155                 160

Glu Ser Lys Tyr Gly Pro Pro Cys Pro Ser Cys Pro Ala Pro Glu Phe
                165                 170                 175

Leu Gly Gly Pro Ser Val Phe Leu Phe Pro Pro Lys Pro Lys Asp Thr
            180                 185                 190

Leu Met Ile Ser Arg Thr Pro Glu Val Thr Cys Val Val Val Asp Val
        195                 200                 205

Ser Gln Glu Asp Pro Glu Val Gln Phe Asn Trp Tyr Val Asp Gly Val
210                 215                 220

Glu Val His Asn Ala Lys Thr Lys Pro Arg Glu Glu Gln Phe Asn Ser
225                 230                 235                 240

Thr Tyr Arg Val Val Ser Val Leu Thr Val Leu His Gln Asp Trp Leu
            245                 250                 255

Xaa Gly Lys Glu Tyr Lys Cys Lys Val Ser Xaa Lys Gly Leu Pro Ser
            260                 265                 270

Ser Ile Glu Lys Thr Ile Ser Xaa Ala Xaa Gly Gln Pro Arg Glu Pro
        275                 280                 285

Gln Val Tyr Thr Leu Pro Pro Ser Gln Glu Glu Met Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Val Leu Asp Ser Asp Gly Ser Phe Phe Leu Tyr Ser Arg Leu
            340                 345                 350

Thr Val Asp Lys Ser Xaa Trp Gln Glu Gly Asn Val Phe Ser Cys Ser
        355                 360                 365

Val Met His Glu Ala Leu His Asn His Tyr Thr Gln Lys Ser Leu Ser
370                 375                 380

Leu Ser Leu Gly Lys
385

<210> SEQ ID NO 17
<211> LENGTH: 574
```

```
<212> TYPE: PRT
<213> ORGANISM: Homo sapiens

<400> SEQUENCE: 17

Met Asp Trp Thr Trp Ile Leu Phe Leu Val Ala Ala Thr Arg Val
1               5                   10                  15

His Ser Gln Thr Gln Leu Val Gln Ser Gly Ala Glu Val Arg Lys Pro
                20                  25                  30

Gly Ala Ser Val Arg Val Ser Cys Lys Ala Ser Gly Tyr Thr Phe Ile
            35                  40                  45

Asp Ser Tyr Ile His Trp Ile Arg Gln Ala Pro Gly His Gly Leu Glu
        50                  55                  60

Trp Val Gly Trp Ile Asn Pro Asn Ser Gly Thr Asn Tyr Ala Pro
65              70                  75                  80

Arg Phe Gln Gly Arg Val Thr Met Thr Arg Asp Ala Ser Phe Ser Thr
                85                  90                  95

Ala Tyr Met Asp Leu Arg Ser Leu Arg Ser Asp Asp Ser Ala Val Phe
            100                 105                 110

Tyr Cys Ala Lys Ser Asp Pro Phe Trp Ser Tyr Tyr Asn Phe Asp
        115                 120                 125

Tyr Ser Tyr Thr Leu Asp Val Trp Gly Gln Gly Thr Thr Val Thr Val
    130                 135                 140

Ser Ser Ala Ser Thr Gln Ser Pro Ser Val Phe Pro Leu Thr Arg Cys
145                 150                 155                 160

Cys Lys Asn Ile Pro Ser Asn Ala Thr Ser Val Thr Leu Gly Cys Leu
                165                 170                 175

Ala Thr Gly Tyr Phe Pro Glu Pro Val Met Val Thr Trp Asp Thr Gly
            180                 185                 190

Ser Leu Asn Gly Thr Thr Met Thr Leu Pro Ala Thr Thr Leu Thr Leu
        195                 200                 205

Ser Gly His Tyr Ala Thr Ile Ser Leu Leu Thr Val Ser Gly Ala Trp
    210                 215                 220

Ala Lys Gln Met Phe Thr Cys Arg Val Ala His Thr Pro Ser Ser Thr
225                 230                 235                 240

Asp Trp Val Asp Asn Lys Thr Phe Ser Val Cys Ser Arg Asp Phe Thr
                245                 250                 255

Pro Pro Thr Val Lys Ile Leu Gln Ser Ser Cys Asp Gly Gly Gly His
            260                 265                 270

Phe Pro Pro Thr Ile Gln Leu Leu Cys Leu Val Ser Gly Tyr Thr Pro
        275                 280                 285

Gly Thr Ile Asn Ile Thr Trp Leu Glu Asp Gly Gln Val Met Asp Val
    290                 295                 300

Asp Leu Ser Thr Ala Ser Thr Thr Gln Glu Gly Glu Leu Ala Ser Thr
305                 310                 315                 320

Gln Ser Glu Leu Thr Leu Ser Gln Lys His Trp Leu Ser Asp Arg Thr
                325                 330                 335

Tyr Thr Cys Gln Val Thr Tyr Gln Gly His Thr Phe Glu Asp Ser Thr
            340                 345                 350

Lys Lys Cys Ala Asp Ser Asn Pro Arg Gly Val Ser Ala Tyr Leu Ser
        355                 360                 365

Arg Pro Ser Pro Phe Asp Leu Phe Ile Arg Lys Ser Pro Thr Ile Thr
    370                 375                 380

Cys Leu Val Val Asp Leu Ala Pro Ser Lys Gly Thr Val Asn Leu Thr
385                 390                 395                 400
```

```
Trp Ser Arg Ala Ser Gly Lys Pro Val Asn His Ser Thr Arg Lys Glu
                405                 410                 415

Glu Lys Gln Arg Asn Gly Thr Leu Thr Val Thr Ser Thr Leu Pro Val
            420                 425                 430

Gly Thr Arg Asp Trp Ile Glu Gly Glu Thr Tyr Gln Cys Arg Val Thr
        435                 440                 445

His Pro His Leu Pro Arg Ala Leu Met Arg Ser Thr Thr Lys Thr Ser
450                 455                 460

Gly Pro Arg Ala Ala Pro Glu Val Tyr Ala Phe Ala Thr Pro Glu Trp
465                 470                 475                 480

Pro Gly Ser Arg Asp Lys Arg Thr Leu Ala Cys Leu Ile Gln Asn Phe
                485                 490                 495

Met Pro Glu Asp Ile Ser Val Gln Trp Leu His Asn Glu Val Gln Leu
            500                 505                 510

Pro Asp Ala Arg His Ser Thr Thr Gln Pro Arg Lys Thr Lys Gly Ser
        515                 520                 525

Gly Phe Phe Val Phe Ser Arg Leu Glu Val Thr Arg Ala Glu Trp Glu
530                 535                 540

Gln Lys Asp Glu Phe Ile Cys Arg Ala Val His Glu Ala Ala Ser Pro
545                 550                 555                 560

Ser Gln Thr Val Gln Arg Ala Val Ser Val Asn Pro Gly Lys
                565                 570

<210> SEQ ID NO 18
<211> LENGTH: 353
<212> TYPE: PRT
<213> ORGANISM: Homo sapiens

<400> SEQUENCE: 18

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
                165                 170                 175

Arg Asp Leu Cys Gly Cys Tyr Ser Val Ser Ser Val Leu Ser Gly Cys
            180                 185                 190

Ala Glu Pro Trp Asn His Gly Lys Thr Phe Thr Cys Thr Ala Ala Tyr
```

```
                195                 200                 205
Pro Glu Ser Lys Thr Pro Leu Thr Ala Thr Leu Ser Lys Ser Gly Asn
210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 19
<211> LENGTH: 258
<212> TYPE: PRT
<213> ORGANISM: Homo sapiens

<400> SEQUENCE: 19

Arg Ser Asp Lys Lys Val Glu Pro Lys Ser Asp Lys Thr His Thr
1               5                   10                  15

Cys Pro Pro Cys Pro Ala Pro Glu Leu Leu Gly Gly Pro Ser Val Phe
                20                  25                  30

Leu Phe Pro Pro Lys Pro Lys Asp Thr Leu Met Ile Ser Arg Thr Pro
            35                  40                  45

Glu Val Thr Cys Val Val Val Asp Val Ser His Glu Asp Pro Glu Val
        50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
```

```
                    210                 215                 220
Asn His Tyr Thr Gln Lys Ser Leu Ser Leu Ser Pro Glu Leu Gln Leu
225                 230                 235                 240

Glu Glu Ser Cys Ala Glu Ala Gln Asp Gly Glu Leu Asp Gly Leu Trp
                245                 250                 255

Thr Thr
```